(12) United States Patent
Brown et al.

(10) Patent No.: US 6,210,964 B1
(45) Date of Patent: Apr. 3, 2001

(54) AVIAN EXTRACELLULAR CALCIUM-SENSING RECEPTOR

(75) Inventors: Edward M. Brown, Milton; Ruben Diaz, Boston; Mei Bai, Brookline; Stephen J. Quinn, Sudbury, all of MA (US)

(73) Assignee: The Brigham and Women's Hospital, Inc., Boston, MA (US)

(*) Notice: Subject to any disclaimer, the term of this patent is extended or adjusted under 35 U.S.C. 154(b) by 0 days.

(21) Appl. No.: 09/134,513

(22) Filed: Aug. 14, 1998

Related U.S. Application Data
(60) Provisional application No. 60/058,095, filed on Aug. 18, 1997.

(51) Int. Cl.$^7$ .......................... C07H 21/04; C12N 15/63; C12N 15/85; C12N 15/86

(52) U.S. Cl. .................. 435/325; 435/320.1; 435/252.3; 536/23.1; 536/23.5

(58) Field of Search ................................. 536/23.1, 23.5; 435/320.1, 325, 252.1, 252.3

(56) References Cited

FOREIGN PATENT DOCUMENTS

9612697 * 5/1996 (WO) ........................... C07C/211/27

OTHER PUBLICATIONS

Aida, et al., "Familial Hypocalciuric Hypercalcemia Associated with Mutation in the Human $Ca^{2+}$–Sensing Receptor Gene," *J. Clin. Endocrin. and Metab.* 80:2594–2598 (1995).
Bradley, et al., "Formulation of Germ–Line Chimaeres from Embryo–Derived Teratocarcinoma Cell Lines," *Nature* 309:255–256 (1984).
Brown, et al., "Cloning and Characterization of an Extracellular $Ca^{2+}$–Sensing Receptor from Bovine Parathyroid," *Nature* 366:575–580 (1993).
Brown, et al., "Calcium Ions as Extracellular Messengers," *Cell* 83:679–682 (1995).
Capecchi, et al., "The New Mouse Genetics: Altering the Genome by Gene Targeting," *Trends in Genetics* 5:70–76 (1989).
Carsience, et al., "Germline Chimeric Chickens from Dispersed Donor Blastodermal Cells and Compromised Recipient Embryos," *Development* 117:669–675 (1993).
Crittenden, et al., "Expression of Retroviral Genes in Transgenic Chickens," *J. Reprod. Fert. Suppl.* 41:163–171 (1990).
Doetschman, et al., "Targetted Correction of a Mutant HPRT Gene in Mouse Embryonic Stem Cells," *Nature* 330:576–578 (1987).
Fliegel, et al., "Amino Acid Sequence of Rabbit Fast–Twitch Skeletal Muscle Calsequestrin Deduced from cDNA and Peptide Sequencing," *Proc. Natl. Acad. Sci. USA* 84:1167–1171 (1987).
Garrett, et al., "Calcitonin–Secreting Cells of the Thyroid Express an Extracellular Calcium Receptor Gene," *Endocrinology* 136:5202–5211 (1995).
Love, et al., "Transgenic Birds by DNA Microinjection," *Biotechnology* 12:60–63 (1994).
Mansour, et al., "Disruption of the Proto–Oncogene int–2 in Mouse Embryo–Derived Stem Cells: A General Strategy for Targeting Mutations to Non–Selectable Genes," *Nature* 336:348–352 (1988).
Nakanishi, "Molecular Diversity of Glutamate Receptors and Implications for Brain Function," *Science* 258:597–603 (1992).
Pollak, et al., "Mutations in the Human $Ca^{2+}$–Sensing Receptor Gene Cause Familial Hypocalciuric Hypercalcemia and Neonatal Severe Hyperparathyroidism," *Cell* 75:1297–1303 (1993).
Pollak, et al., "Familial Hypocalciuric Hypercalcemia and Neonatal Severe Hyperparathyroidism, Effects of Mutant Gene Dosage on Phenotype," *J. Clin. Invest.* 93:1108–1112 (1994).
Pollak, et al., "Autosomal Dominant Hypocalcaemia Caused by a $Ca^{2+}$–Sensing Receptor Gene Mutation," *Nature Genetics* 8:303–307 (1994).
Riccardi, et al., "Cloning and Functional Expression of a Rat Kidney Extracellular Calcium/Polyvalent Cation–Sensing Receptor," *Proc. Natl. Acad. Sci. USA* 92:131–135 (1995).
Ruat, et al., "Calcium Sensing Receptor: Molecular Cloning in Rat and Localization to Nerve Terminals," *Proc. Natl. Acad. Sci. USA* 92:3161–3165 (1995).
Salter, et al., "Transgenic Chickens: Insertion of Retroviral Genes into the Chicken Germ Line," *Virology* 157:236–240 (1987).
Thomas, et al., "Site–Directed Mutagenesis by Gene Targeting in Mouse Embryo–Derived Stem Cells," *Cell* 51:503–512 (1987).
Wang, et al., "β Opiate Receptor: cDNA Cloning and Expression," *Proc. Natl. Acad. Sci. USA* 90:10230–10234 (1993).
Ye, et al., "Modulation by Polycationic $Ca^{2+}$–Sensing Receptor Agonists of Nonselective Cation Channels in Rat Hippocampal Neurons," *Biochem. Biophys. Res. Comm.* 224:271–280 (1996).
Ye, et al., "Agonists of the $Ca^{2+}$–Sensing Receptor (CaR) Activate Nonselective Cation Channels in HEK293 Cells Stably Transfected with the Human CaR," *Biochem Biophys. Res. Comm.* 226:572–579 (1996).

* cited by examiner

Primary Examiner—John L. LeGuyader
Assistant Examiner—Michael C. Wilson
(74) Attorney, Agent, or Firm—Michael A. Sanzo; Pillsbury Winthrop LLP

(57) ABSTRACT

The present invention is directed to an avian calcium-sensing receptor and to DNA sequences which encode the receptor. In addition, the invention is directed to methods and compositions which serve to modulate the serum concentration of calcium in humans and animals.

10 Claims, 26 Drawing Sheets

FIG.1a
FIG.1b
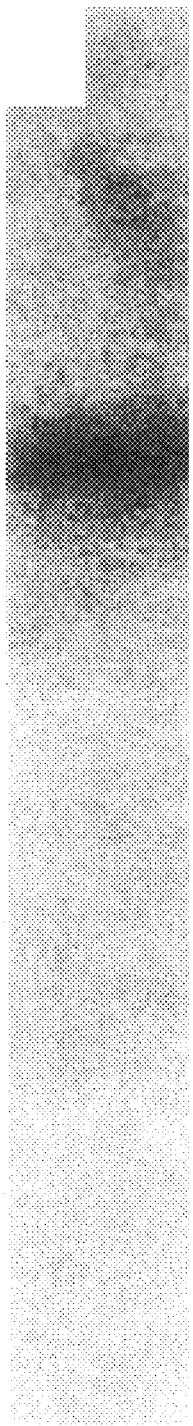
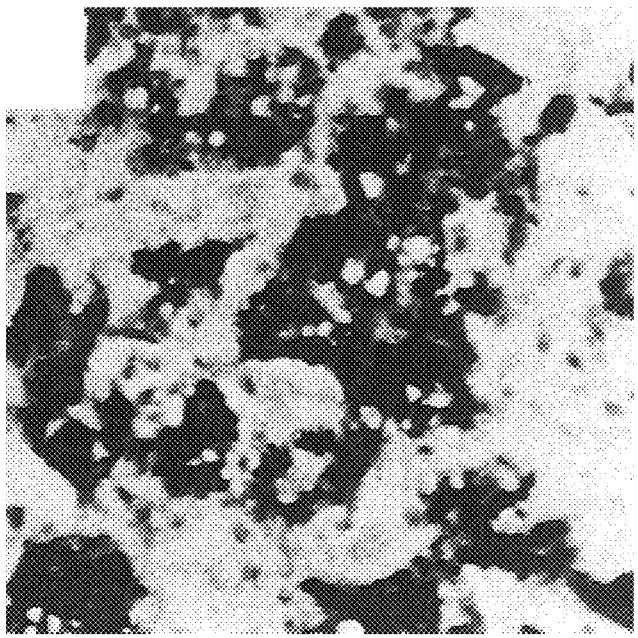
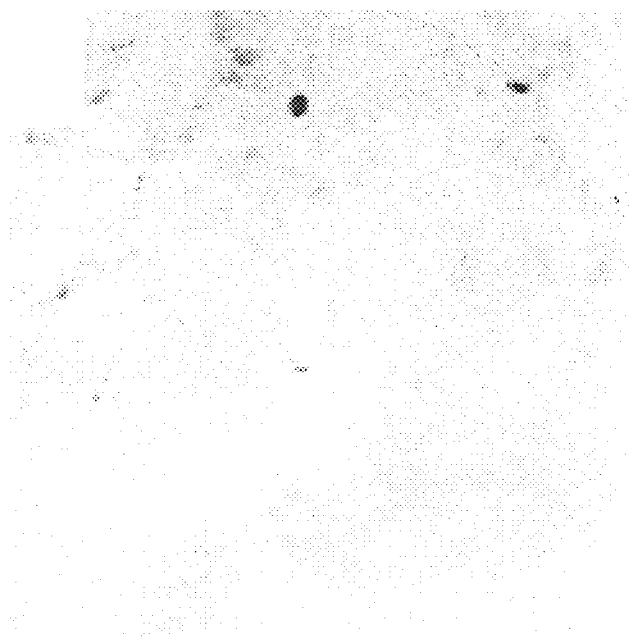
FIG.1c

```
gtcgacccacgcgtccgcaa  catccgctttcttacatcgt  cttttccaattttacatcct
ataaccccttggtgaaagga  ggaacaATGACTTTATATAG  CTGCTGTTTGATTCTTTTGC  120
                         M  T  L  Y  S     C  C  L  I  L  L  L     12
TGTTTACCTGGAACACTGCT  GCCTATGGGCCAAACCAACG  GGCACAGAAGAAGGGAGACA  180
 F  T  W  N  T  A     A  Y  G  P  N  Q  R   A  Q  K  K  G  D  I    32
TTATTCTTGGAGGATTGTTC  CCCATCCATTTTGGAGTGGC  TGCTAAAGACCAGGATCTAA  240
 I  L  G  G  L  F     P  I  H  F  G  V  A   A  K  D  Q  D  L  K    52
AGTCAAGACCCGAATCAGTG  GAGTGCATAAGGTATAATTT  CCGAGGCTTCCGCTGGCTCC  300
 S  R  P  E  S  V     E  C  I  R  Y  N  F   R  G  F  R  W  L  Q    72
AGGCTATGATCTTTGCCATA  GAAGAAATAAATAATAGCCC  AAATCTCCTTCCCAACATGA  360
 A  M  I  F  A  I     E  E  I  N  N  S  P   N  L  L  P  N  M  T    92
CCTTGGGATACAGGATATTT  GACACTTGCAATACAGTCTC  TAAAGCCCTTGAGGCCACTC  420
 L  G  Y  R  I  F     D  T  C  N  T  V  S   K  A  L  E  A  T  L   112
TGAGTTTTGTGGCCCAGAAC  AAGATAGACTCCTTGAACCT  GGATGAATTCTGCAACTGCT  480
 S  F  V  A  Q  N     K  I  D  S  L  N  L   D  E  F  C  N  C  S   132
CAGAACATATCCCTTCCACC  ATTGCAGTCGTGGGGGCAAC  CGGCTCTGGGGTTTCCACCG  540
 E  H  I  P  S  T     I  A  V  V  G  A  T   G  S  G  V  S  T  A   152
CTGTGGCCAATCTGCTGGGA  CTCTTTTACATACCTCAGGT  CAGCTATGCCTCATCCAGTC  600
 V  A  N  L  L  G     L  F  Y  I  P  Q  V   S  Y  A  S  S  S  R   172
GTCTCTTGAGCAACAAGAAC  CAGTTCAAGTCCTTCCTCCG  CACAATCCCCAATGACGAGC  660
 L  L  S  N  K  N     Q  F  K  S  F  L  R   T  I  P  N  D  E  H   192
ATCAGGCCACTGCGATGGCA  GACATCATCGAGTACTTCCG  CTGGAACTGGGTGGGAACGA  720
 Q  A  T  A  M  A     D  I  I  E  Y  F  R   W  N  W  V  G  T  I   212
TTGCAGCTGATGATGACTAT  GGCCGGCCAGGGATTGAAAA  GTTTCGGGAGGAGGCGGAGG  780
 A  A  D  D  D  Y     G  R  P  G  I  E  K   F  R  E  E  A  E  E   232
AGAGAGATATCTGCATTGAT  TTTAGTGAGCTCATCTCCCA  GTACTCAGATGAAGAAGAGA  840
 R  D  I  C  I  D     F  S  E  L  I  S  Q   Y  S  D  E  E  E  I   252
TTCAGCAGGTGGTGGAGGTC  ATCCAGAACTCCACAGCACG  AGTGATTGTGGTTTTCTCCA  900
 Q  Q  V  V  E  V     I  Q  N  S  T  A  R   V  I  V  V  F  S  S   272
GTGGACCAGACCTGGAACCC  CTCATCAAAGAGATTGTCAG  GCGAAACATCACTGGAAAGA  960
 G  P  D  L  E  P     L  I  K  E  I  V  R   R  N  I  T  G  K  I   292
TCTGGCTGGCAAGTGAAGCC  TGGGCCAGTTCATCCCTGAT  AGCCATGCCAGAGTTCTTCC  1020
 W  L  A  S  E  A     W  A  S  S  S  L  I   A  M  P  E  F  F  R   312
GTGTCATCGGCAGCACCATT  GGGTTTGCACTGAAGGCAGG  CCAGATCCCAGGCTTTCGCG  1080
 V  I  G  S  T  I     G  F  A  L  K  A  G   Q  I  P  G  F  R  E   332
AGTTCCTGCAGAAGGTGCAT  CCCAAAAAGTCTGCCAACAA  TGGATTTGCCAAGGAGTTTT  1140
 F  L  Q  K  V  H     P  K  K  S  A  N  N   G  F  A  K  E  F  W   352
GGGAAGAGACATTTAACTGC  TATCTCCCCAGTGAGTCCAA  AAATTCTCCAGCTTCAGCTT  1200
 E  E  T  F  N  C     Y  L  P  S  E  S  K   N  S  P  A  S  A  S   372
CCTTCCACAAGGCCCACGAA  GAGGGCTTGGGAGCTGGAAA  TGGTACAGCTGCCTTCCGAC  1260
 F  H  K  A  H  E     E  G  L  G  A  G  N   G  T  A  A  F  R  P   392
```

FIG.2a

```
CTCCATGCACAGGTGATGAG AACATCACCAGTGTGGAAAC ACCGTACATGGACTTCACAC 1320
   P  C  T  G  D  E    N  I  T  S  V  E  T    P  Y  M  D  F  T  H   412
ACTTGCGGATATCCTATAAT GTATATTTGGCAGTATATTC TATTGCTCACGCTTTGCAGG 1380
   L  R  I  S  Y  N    V  Y  L  A  V  Y  S    I  A  H  A  L  Q  D   432
ATATATATACTTGTACCCCT GGGAAAGGACTCTTCACCAA CGGATCCTGTGCAGACATTA 1440
   I  Y  T  C  T  P    G  K  G  L  F  T  N    G  S  C  A  D  I  K   452
AGAAGGTTGAGGCATGGCAG GTTCTGAAGCACCTGCGCCA CTTAAATTTCACCAGTAACA 1500
   K  V  E  A  W  Q    V  L  K  H  L  R  H    L  N  F  T  S  N  M   472
TGGGGGAGCAAGTGGACTTT GATGAGTTTGGAGACCTGGT GGGGAATTACTCAATAATCA 1560
   G  E  Q  V  D  F    D  E  F  G  D  L  V    G  N  Y  S  I  I  N   492
ACTGGCATCTCTCTCCAGAG GATGGCTCAGTCGTCTTTGA GGAGGTTGGGCACTACAATG 1620
   W  H  L  S  P  E    D  G  S  V  V  F  E    E  V  G  H  Y  N  V   512
TGTATGCCAAGAAAGGGGAG AGGCTCTTTATCAATGAAAA CAAAATCCTGTGGAGTGGAT 1680
   Y  A  K  K  G  E    R  L  F  I  N  E  N    K  I  L  W  S  G  F   532
TCTCAAAGGAGGTGCCCTTC TCTAACTGCAGCAGGGACTG CCTGCCAGGCACCAGGAAGG 1740
   S  K  E  V  P  F    S  N  C  S  R  D  C    L  P  G  T  R  K  G   552
GCATTATTGAGGGAGAGCCC ACTTGCTGCTTCGAGTGTGT GGACTGCCCTGATGGGGAGT 1800
   I  I  E  G  E  P    T  C  C  F  E  C  V    D  C  P  D  G  E  Y   572
ACAGTGATGAAACAGATGCA AGTGCTTGTGACAAGTGCCC TGAGGATTACTGGTCTAATG 1860
   S  D  E  T  D  A    S  A  C  D  K  C  P    E  D  Y  W  S  N  E   592
AGAACCACACATCCTGCATC CCCAAGCAGATAGAGTTTCT ATCCTGGACAGAGCCCTTTG 1920
   N  H  T  S  C  I    P  K  Q  I  E  F  L    S  W  T  E  P  F  G   612
GAATCGCTTTAACTCTCTTT GCTGTGCTGGGAATTTTCCT GACTTCTTTTGTCCTGGGAG 1980
   I  A  L  T  L  F    A  V  L  G  I  F  L    T  S  F  V  L  G  V   632
TCTTCACCAAATTTCGCAAC ACTCCCATCGTCAAGGCCAC AAACCGGGAGCTGTCCTACC 2040
   F  T  K  F  R  N    T  P  I  V  K  A  T    N  R  E  L  S  Y  L   652
TCCTCCTCTTCTCCTTGCTC TGCTGCTTCTCTAGCTCATT GTTCTTCATTGGAGAGCCAC 2100
   L  L  F  S  L  L    C  C  F  S  S  S  L    F  F  I  G  E  P  Q   672
AGAACTGGACTTGCCGTCTG CGGCAGCCAGCTTTTGGCAT CAGCTTTGTCCTCTGCATCT 2160
   N  W  T  C  R  L    R  Q  P  A  F  G  I    S  F  V  L  C  I  S   692
CCTGCATCCTGGTGAAAACC AATCGTGTCCTGCTTGTCTT CGAGGCAAAGATCCCTACAA 2220
   C  I  L  V  K  T    N  R  V  L  L  V  F    E  A  K  I  P  T  S   712
GCCTCCACCGAAAATGGTGG GGCCTCAACCTCCAGTTCCT CCTGGTCTTCTTGTGCACAT 2280
   L  H  R  K  W  W    G  L  N  L  Q  F  L    L  V  F  L  C  T  F   732
TTGTGCAGATTGTCATCTGC GTGATTTGGCTCTACACGGC CCCACCATCCAGTTATCGAA 2340
   V  Q  I  V  I  C    V  I  W  L  Y  T  A    P  P  S  S  Y  R  N   752
ACCATGAGCTGGAGGATGAG ATTATCTTCATCACCTGCCA TGAAGGCTCCTTGATGGCCC 2400
   H  E  L  E  D  E    I  I  F  I  T  C  H    E  G  S  L  M  A  L   772
TTGGCTTCCTCATTGGCTAC ACCTGTCTCCTGGCAGCCAT CTGCTTCTTCTTTGCCTTTA 2460
   G  F  L  I  G  Y    T  C  L  L  A  A  I    C  F  F  F  A  F  K   792
```

FIG.2b

```
AGTCTCGAAAACTGCCTGAG  AACTTCAATGAGGCCAAGTT  CATCACCTTCAGCATGCTGA  2520
  S  R  K  L  P  E     N  F  N  E  A  K  F     I  T  F  S  M  L  I      812
TCTTCTTCATTGTCTGGATC  TCCTTCATCCCTGCTTACGC  CAGCACATATGGCAAATTTG  2580
  F  F  I  V  W  I     S  F  I  P  A  Y  A     S  T  Y  G  K  F  V      832
TCTCTGCTGTGGAGGTGATT  GCAATACTGGCTGCCAGTTT  TGGGCTTCTGGCCTGCATCT  2640
  S  A  V  E  V  I     A  I  L  A  A  S  F     G  L  L  A  C  I  F      852
TCTTTAACAAAGTCTACATC  ATCCTCTTCAAGCCTTCCCG  CAACACAATCGAGGAGGTGC  2700
  F  N  K  V  Y  I     I  L  F  K  P  S  R     N  T  I  E  E  V  R      872
GCTGCAGCACAGCTGCCCAC  GCTTTCAAGGTGGCCGCCAG  GGCCACGCTGAGACGCAGCA  2760
  C  S  T  A  A  H     A  F  K  V  A  A  R     A  T  L  R  R  S  N      892
ATGTGTCACGCAAGCGTTCC  AACAGCCTCGGAGGTTCCAC  CGGTTCCACCCCATCCTCCT  2820
  V  S  R  K  R  S     N  S  L  G  G  S  T     G  S  T  P  S  S  S      912
CCATCAGCAGCAAGAGCAAC  CATGAAGACCCTTTTCCTCT  ACCGGCTTCTGCTGAGCGGC  2880
  I  S  S  K  S  N     H  E  D  P  F  P  L     P  A  S  A  E  R  Q      932
AGCGGCAGCAGCAGCGTGGG  TGCAAGCAGAAGGTCAGCTT  TGGGAGTGGTACGGTCACCT  2940
  R  Q  Q  Q  R  G     C  K  Q  K  V  S  F     G  S  G  T  V  T  L      952
TGTCACTGAGTTTTGAGGAG  CCACAGAAGAACGCCATGGC  CAACAGGAACGCCAAGCGCA  3000
  S  L  S  F  E  E     P  Q  K  N  A  M  A     N  R  N  A  K  R  R      972
GGAACTCCCTGGAGGCCCAG  AACAGCGATGACAGCCTGAT  GCGGCACAGGGCCCTGCTCG  3060
  N  S  L  E  A  Q     N  S  D  D  S  L  M     R  H  R  A  L  L  A      992
CTCTACAGAACAGCGAGTCC  CTCAGTGCCGAGCCTGGCTT  CCAGACAGCATCCAGCCCAG  3120
  L  Q  N  S  E  S     L  S  A  E  P  G  F     Q  T  A  S  S  P  E     1012
AGACCAGTTCACAGGAGTCG  GTAGTGGGAGACAACAAAGA  AGAGGTACCAAACCCTGAGG  3180
  T  S  S  Q  E  S     V  V  G  D  N  K  E     E  V  P  N  P  E  A     1032
CAGAGCCCTCCCTGCCGTCA  GCTAACTCCCGAAATTTTAT  AGGCACTGGAGGCAGCTCTG  3240
  E  P  S  L  P  S     A  N  S  R  N  F  I     G  T  G  G  S  S  V     1052
TCACAGAAAACACAGTACAT  TCCtaacaaaagaaggtcat  gaaaagcacttccccaggag  3300
  T  E  N  T  V  H     S                                                1059
gaacttgctcacctcttgct  tctgaatgggaaagacaaca  aagatacatatctgtgacac  3360
agtcccaccacacattgttg  ctatcaccagcagggtaaaa  cacgtgcctccagaggaaag  3420
actaccagaagcctgtgtgt  ggggagcctcaaactgaatt  tgcagttgctttactgaaat  3480
caggacacgtggggaggaca  agtgaagattgcctctggtg  gggctttaagtagaactctg  3540
catattgtcttgcctctgta  agcttttcctgccagactgc  aactcagctgactatgggag  3600
gcactgagcaattccactat  actctgcttttacatttatg  tataatattcctcttttccca  3660
ctatgtataatattccctct  ttatccagtatatgtgatct  gtaaccacgtgcatcaggac  3720
tctcagctcttcaaaagcaa  gacacacggtttcacttggg  gaaagcacggtcattgggaa  3780
aataaaaaagccccaacat   cctgcatgctgtgtacagcc  aagggtgtgaacatgtaaag  3840
tatttaatgtgacagagcac  cctgctatttatatttagta  atgtcccaatttctcctctc  3900
tgcccagcaggaaatactgg  acaatacccttcatagactc  cattgcactagaccaagcta  3960
ctaggttcctactggtttct  tccagcagatgtagctttac  ctccagcctgcctgctttgg  4000
```

FIG.2c

```
tggaaggggagaacaggttg taaatccccctggagattgc tgcgagagcacaatgagatg 4060
tattcgtgattgattatgtc gctagtagttgtatgcttaa caaagtgttgctgctgtaat 4120
attccacatggcatacgtgg ctaacccttccacaccatag tcagtgttgtgctttgccat 4180
attaatccgcctcataccca cacatagcattgcgctggtt gtgacaatacttgtgggcct 4240
gatacaaagccaatgaaaca aggtgaaatggagaaatagc ccccaaatttgataatattt 4300
gagatgagtattgcaagtgt gcatggtggtagaggatgga gtaaataaaacatacagagt 4360
tgggctctgagacgtgcaaa cagacaaatgagtaaattgg atgtttggttcctgtaggcc 4420
ttcaagtaggttatgtccct gttggcccatcttgaagaga cagtacctaaacaagaagag 4480
tgcactgtgccttggtgaga gtaaggacttcaaaagagag cacatcagaacttcattagt 4540
cttggctcttgttcagcacc ccaaaagtagacataagtgc tcctgactgtgcacgatgtg 4600
cccggttcctctgcattctg cgaatgttgaagtaagagag tccttagaacagatttctgt 4660
tgcagcctgaagaaagaaag agtgaccctaggcaacttgg caggaagggcaaggttattc 4720
tgtagaatttacttccctct tcccagatcccatatgcaag aacaggtatttgtcatgagg 4780
atatcagtacctgccctcat cacacacagaggcactctag accactgcggaaaggtatat 4840
aggcctgctacttattgtga atggagatgaaaggactgtt gtgaatgtgatggggaaaat 4900
accacaattctcttgttact gttttgcttggttgatgtt ttgtgttttgtgtggtttt 4960
tttctcgccagagcaggaaa ataaaacttacaggtgacat tactgcataaaaaaaaaaa 5020
aaaaaa
```

FIG.2d

| | | |
|---|---|---|
| HuPCaR | MARYSCCWVLLALTWHTSAYGPOQRAQKKGDIILGGLFPIHFGVAAKQDLKSRPESVECIRYNFRGFRWLQAMIFAIEEINSSPALLPNLTLGYRIFDT | 100 |
| ChPCaR | MTLYSCCLILLLPTWNTAAYGPNQRAQKKGDIILGGLFPIHFGVAAKQDLKSRPESVECIRYNFRGFRWLQAMIFAIEEINNSPNLLPNMTLGYRIFDT | 100 |
| HuPCaR | CNTVSKALEATLSFVAQNKIDSLNLDEFCNCSEHIPSTIAVWGATGSGVSTAVANLLGLFYIPQVSYASSSRLLSNKNQFKSFLRTIPNDEHQATAMADI | 200 |
| ChPCaR | CNTVSKALEATLSFVAQNKIDSLNLDEFCNCSEHIPSTIAVWGATGSGVSTAVANLLGLFYIPQVSYASSSRLLSNKNQFKSFLRTIPNDEHQATAMADI | 200 |
| HuPCaR | IEYFRMNWGTIAADDDYGRPGIEKFREEAEERDICIDFSELISQYSDEEEIQWVEVIQNSTAKVIVWFSSGPDLEPLIKEIVRRNITGKIWLASEAWA | 300 |
| ChPCaR | IEYFRMNWGTIAADDDYGRPGIEKFREEAEERDICIDFSELISQYSDEEEIQWVEVIQNSTAKVIVWFSSGPDLEPLIKEIVRRNITGKIWLASEAWA | 300 |
| HuPCaR | SSSLIAMPQYFHMGGTIGFALKAGQIPGFREFLKKVHPPKSVHNGFAKEFWEETFNCHLDEGAKGPLPVDTFLRGHEESGDRFSNSSTAFRPLCTGDEN | 400 |
| ChPCaR | SSSLIAMPERPMIGSTIGFALKAGQIPGFREFLDKVHPKKSANNGFAKEFWEETFNCMLPSESQNSPASASFHKAHEEGLGA-GNGTAAFRPPCTGDEN | 399 |
| HuPCaR | ISSVETPYIQVTHLRISYNVYLAVYSIAHALQDIYTCLPGPGLFTNGSCADIKKVEAWQVLKHLRHLNFTNNMGEQVIFDECGDLVGNYSIINWHLSPED | 500 |
| ChPCaR | IDSVETPYMQRTHLRISYNVYLAVYSIAHALQDIYTCIPGKGLFTNGSCADIKKVEAWQVLKHLRHLNFTSNMGEQVCFDEFGDLVGNYSIINWHLSPED | 499 |
| HuPCaR | GSIVFKEVGYYNVYAKKGERLFINEEKILWSGFSREVPFSNCSRDCLAGTRKGIIEGEPTCCFECVECPDGEYSDETDASAQNKCPDQWSNENHTSCIA | 600 |
| ChPCaR | GSWVFEEVGHYNVYAKKGERLFINEVKILWSGFSKEVPFSNCSRDCLEGTRKGIIEGEPTCCFECVCCPDGEYSDETDASACQKCPEDYWSNENHTSCIP | 599 |
| HuPCaR | KELEFLSWTEPFGIALTLFAVLGIFLTAFVLGVFIKFRNTPIVKAINRELSYLLLFSLLCCFSSSLFFIGEPQWTCRLRQPAFGISFVLCISCILVKTN | 700 |
| ChPCaR | KCLEFLSWTEPFGIALTLFAVLGIFLTSFVLGVFDKFRNTPIVKAINRELSYLLLFSLLCCFSSSLFFIGEPQWTCRLRQPAFGISFVLCISCILVKTN | 699 |
| HuPCaR | RVLLVFEAKIPTSFHRKWMGLNLQFLLVFLCTFMQIVCVIWLYTAPPSSYRNQELEDEIIFITCHEGSLMALGFLIGYTCLLAAICFFFAFKSRKLPEN | 800 |
| ChPCaR | RVLLVFEAKIPTSLHRKWMGLNLQFLLVFLCTFVQIVCVIWLYTAPPSSYRNHELEDEIIFITCHEGSLMALGFLIGYTCLLAAICFFFAFKSRKLPEN | 799 |
| HuPCaR | FNEAKFITFSMLIFFIVWISFIPAYASTYGKFVSAVEVIAILAASFGLLACIFFNKIYTILFKPSRNTIEEVRCSTAAHAFKVAARATLRRSNVSRKRSS | 900 |
| ChPCaR | FNEAKFITFSMLIFFIVWISFIPAYASTYGKFVSAVEVIAILAASFGLLACIFFNKMYIILFKPSRNTIEEVRCSTAAHAFKVAARATLRRSNVSRKRSN | 899 |

FIG.4a

```
HuPCaR  SLGGSTGSTPSSSISSKSNSEDPFPQPERQKQQQPLTLPQQQRSQQQPRCKQKVIFGSGTVTPSLSFCEPQKNAMAHQNSTHQNSLEA 1000
ChPCaR  SLGGSTGSTPSSSISSKSN-EDPFPLPAS----------AEPQRQQQRG-CKQKVSFGSGTVTLSLSFEEPQKNAMANRNAKRRNSLEA  977

HuPCaR  QKSSDILDRHQELLEQCGETDLDLTVQETGLQCPVGDQRPEVEDPEEL-SP----ALVWSSSQSFVISGGGSIVTENMMS         1078
ChPCaR  QNSDDSLMRHRALLALQNSESLSAEPGFQTASSPETSSQESVVGDNKEEVPNPEAEPSLPSANSRNFIGTGGSSVTENIMHS      1059
```

FIG.4b

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 3177 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (xi) SEQUENCE DESCRIPTION: SEQ ID NO:1:

```
ATGACTTTAT ATAGCTGCTG TTTGATTCTT TTGCTGTTTA CCTGGAACAC TGCTGCCTAT        60

GGGCCAAACC AACGGGCACA GAAGAAGGGA GACATTATTC TTGGAGGATT GTTCCCCATC       120

CATTTTGGAG TGGCTGCTAA AGACCAGGAT CTAAAGTCAA GACCCGAATC AGTGGAGTGC       180

ATAAGGTATA ATTTCCGAGG CTTCCGCTGG CTCCAGGCTA TGATCTTTGC CATAGAAGAA       240

ATAAATAATA GCCCAAATCT CCTTCCCAAC ATGACCTTGG GATACAGGAT ATTTGACACT       300

TGCAATACAG TCTCTAAAGC CCTTGAGGCC ACTCTGAGTT TTGTGGCCCA GAACAAGATA       360

GACTCCTTGA ACCTGGATGA ATTCTGCAAC TGCTCAGAAC ATATCCCTTC CACCATTGCA       420

GTCGTGGGGG CAACCGGCTC TGGGGTTTCC ACCGCTGTGG CCAATCTGCT GGGACTCTTT       480

TACATACCTC AGGTCAGCTA TGCCTCATCC AGTCGTCTCT TGAGCAACAA GAACCAGTTC       540

AAGTCCTTCC TCCGCACAAT CCCCAATGAC GAGCATCAGG CCACTGCGAT GGCAGACATC       600

ATCGAGTACT TCCGCTGGAA CTGGGTGGGA ACGATTGCAG CTGATGATGA CTATGGCCGG       660

CCAGGGATTG AAAAGTTTCG GGAGGAGGCG GAGGAGAGAG ATATCTGCAT TGATTTTAGT       720

GAGCTCATCT CCCAGTACTC AGATGAAGAA GAGATTCAGC AGGTGGTGGA GGTCATCCAG       780

AACTCCACAG CACGAGTGAT TGTGGTTTTC TCCAGTGGAC CAGACCTGGA ACCCCTCATC       840

AAAGAGATTG TCAGGCGAAA CATCACTGGA AAGATCTGGC TGGCAAGTGA AGCCTGGGCC       900

AGTTCATCCC TGATAGCCAT GCCAGAGTTC TTCCGTGTCA TCGGCAGCAC CATTGGGTTT       960

GCACTGAAGG CAGGCCAGAT CCCAGGCTTT CGCGAGTTCC TGCAGAAGGT GCATCCCAAA      1020

AAGTCTGCCA ACAATGGATT TGCCAAGGAG TTTTGGGAAG AGACATTTAA CTGCTATCTC      1080

CCCAGTGAGT CCAAAAATTC TCCAGCTTCA GCTTCCTTCC ACAAGGCCCA CGAAGAGGGC      1140

TTGGGAGCTG GAAATGGTAC AGCTGCCTTC CGACCTCCAT GCACAGGTGA TGAGAACATC      1200

ACCAGTGTGG AAACACCGTA CATGGACTTC ACACACTTGC GGATATCCTA TAATGTATAT      1260

TTGGCAGTAT ATTCTATTGC TCACGCTTTG CAGGATATAT ATACTTGTAC CCCTGGGAAA      1320
```

-continued

```
GGACTCTTCA CCAACGGATC CTGTGCAGAC ATTAAGAAGG TTGAGGCATG GCAGGTTCTG    1380

AAGCACCTGC GCCACTTAAA TTTCACCAGT AACATGGGGG AGCAAGTGGA CTTTGATGAG    1440

TTTGGAGACC TGGTGGGGAA TTACTCAATA ATCAACTGGC ATCTCTCTCC AGAGGATGGC    1500

TCAGTCGTCT TTGAGGAGGT TGGGCACTAC AATGTGTATG CCAAGAAAGG GGAGAGGCTC    1560

TTTATCAATG AAAACAAAAT CCTGTGGAGT GGATTCTCAA AGGAGGTGCC CTTCTCTAAC    1620

TGCAGCAGGG ACTGCCTGCC AGGCACCAGG AAGGGCATTA TTGAGGGAGA GCCCACTTGC    1680

TGCTTCGAGT GTGTGGACTG CCCTGATGGG GAGTACAGTG ATGAAACAGA TGCAAGTGCT    1740

TGTGACAAGT GCCCTGAGGA TTACTGGTCT AATGAGAACC ACACATCCTG CATCCCCAAG    1800

CAGATAGAGT TTCTATCCTG GACAGAGCCC TTTGGAATCG CTTTAACTCT CTTTGCTGTG    1860

CTGGGAATTT TCCTGACTTC TTTTGTCCTG GGAGTCTTCA CCAAATTTCG CAACACTCCC    1920

ATCGTCAAGG CCACAAACCG GGAGCTGTCC TACCTCCTCC TCTTCTCCTT GCTCTGCTGC    1980

TTCTCTAGCT CATTGTTCTT CATTGGAGAG CCACAGAACT GGACTTGCCG TCTGCGGCAG    2040

CCAGCTTTTG GCATCAGCTT TGTCCTCTGC ATCTCCTGCA TCCTGGTGAA AACCAATCGT    2100

GTCCTGCTTG TCTTCGAGGC AAAGATCCCT ACAAGCCTCC ACCGAAAATG GTGGGGCCTC    2160

AACCTCCAGT TCCTCCTGGT CTTCTTGTGC ACATTTGTGC AGATTGTCAT CTGCGTGATT    2220

TGGCTCTACA CGGCCCCACC ATCCAGTTAT CGAAACCATG AGCTGGAGGA TGAGATTATC    2280

TTCATCACCT GCCATGAAGG CTCCTTGATG GCCCTTGGCT TCCTCATTGG CTACACCTGT    2340

CTCCTGGCAG CCATCTGCTT CTTCTTTGCC TTTAAGTCTC GAAAACTGCC TGAGAACTTC    2400

AATGAGGCCA AGTTCATCAC CTTCAGCATG CTGATCTTCT TCATTGTCTG GATCTCCTTC    2460

ATCCCTGCTT ACGCCAGCAC ATATGGCAAA TTTGTCTCTG CTGTGGAGGT GATTGCAATA    2520

CTGGCTGCCA GTTTTGGGCT TCTGGCCTGC ATCTTCTTTA ACAAAGTCTA CATCATCCTC    2580

TTCAAGCCTT CCCGCAACAC AATCGAGGAG GTGCGCTGCA GCACAGCTGC CCACGCTTTC    2640

AAGGTGGCCG CCAGGGCCAC GCTGAGACGC AGCAATGTGT CACGCAAGCG TTCCAACAGC    2700

CTCGGAGGTT CCACCGGTTC CACCCCATCC TCCTCCATCA GCAGCAAGAG CAACCATGAA    2760

GACCCTTTTC CTCTACCGGC TTCTGCTGAG CGGCAGCGGC AGCAGCAGCG TGGGTGCAAG    2820

CAGAAGGTCA GCTTTGGGAG TGGTACGGTC ACCTTGTCAC TGAGTTTTGA GGAGCCACAG    2880

AAGAACGCCA TGGCCAACAG GAACGCCAAG CGCAGGAACT CCCTGGAGGC CCAGAACAGC    2940

GATGACAGCC TGATGCGGCA CAGGGCCCTG CTCGCTCTAC AGAACAGCGA GTCCCTCAGT    3000

GCCGAGCCTG GCTTCCAGAC AGCATCCAGC CCAGAGACCA GTTCACAGGA GTCGGTAGTG    3060

GGAGACAACA AAGAAGAGGT ACCAAACCCT GAGGCAGAGC CCTCCCTGCC GTCAGCTAAC    3120

TCCCGAAATT TTATAGGCAC TGGAGGCAGC TCTGTCACAG AAAACACAGT ACATTCC      3177
```

(2) INFORMATION FOR SEQ ID NO:2:

(i) SEQUENCE CHARACTERISTICS:
        (A) LENGTH: 1059 amino acids
        (B) TYPE: amino acid
        (C) STRANDEDNESS: Not Relevant
        (D) TOPOLOGY: Not Relevant (ii) MOLECULE TYPE: protein (iii) HYPOTHETICAL: NO (xi) SEQUENCE DESCRIPTION: SEQ ID NO:2:

```
Met Thr Leu Tyr Ser Cys Cys Leu Ile Leu Leu Phe Thr Trp Asn
1               5                   10                  15
```

-continued

```
Thr Ala Ala Tyr Gly Pro Asn Gln Arg Ala Gln Lys Lys Gly Asp Ile
             20                  25                  30
Ile Leu Gly Gly Leu Phe Pro Ile His Phe Gly Val Ala Ala Lys Asp
         35                  40                  45
Gln Asp Leu Lys Ser Arg Pro Glu Ser Val Glu Cys Ile Arg Tyr Asn
 50                  55                  60
Phe Arg Gly Phe Arg Trp Leu Gln Ala Met Ile Phe Ala Ile Glu Glu
 65                  70                  75                  80
Ile Asn Asn Ser Pro Asn Leu Leu Pro Asn Met Thr Leu Gly Tyr Arg
                 85                  90                  95
Ile Phe Asp Thr Cys Asn Thr Val Ser Lys Ala Leu Glu Ala Thr Leu
             100                 105                 110
Ser Phe Val Ala Gln Asn Lys Ile Asp Ser Leu Asn Leu Asp Glu Phe
         115                 120                 125
Cys Asn Cys Ser Glu His Ile Pro Ser Thr Ile Ala Val Val Gly Ala
 130                 135                 140
Thr Gly Ser Gly Val Ser Thr Ala Val Ala Asn Leu Leu Gly Leu Phe
145                 150                 155                 160
Tyr Ile Pro Gln Val Ser Tyr Ala Ser Ser Arg Leu Leu Ser Asn
                 165                 170                 175
Lys Asn Gln Phe Lys Ser Phe Leu Arg Thr Ile Pro Asn Asp Glu His
             180                 185                 190
Gln Ala Thr Ala Met Ala Asp Ile Ile Glu Tyr Phe Arg Trp Asn Trp
         195                 200                 205
Val Gly Thr Ile Ala Ala Asp Asp Tyr Gly Arg Pro Gly Ile Glu
 210                 215                 220
Lys Phe Arg Glu Glu Ala Glu Glu Arg Asp Ile Cys Ile Asp Phe Ser
225                 230                 235                 240
Glu Leu Ile Ser Gln Tyr Ser Asp Glu Glu Ile Gln Gln Val Val
                 245                 250                 255
Glu Val Ile Gln Asn Ser Thr Ala Arg Val Ile Val Phe Ser Ser
             260                 265                 270
Gly Pro Asp Leu Glu Pro Leu Ile Lys Glu Ile Val Arg Arg Asn Ile
         275                 280                 285
Thr Gly Lys Ile Trp Leu Ala Ser Glu Ala Trp Ala Ser Ser Ser Leu
 290                 295                 300
Ile Ala Met Pro Glu Phe Phe Arg Val Ile Gly Ser Thr Ile Gly Phe
305                 310                 315                 320
Ala Leu Lys Ala Gly Gln Ile Pro Gly Phe Arg Glu Phe Leu Gln Lys
                 325                 330                 335
Val His Pro Lys Lys Ser Ala Asn Asn Gly Phe Ala Lys Glu Phe Trp
             340                 345                 350
Glu Glu Thr Phe Asn Cys Tyr Leu Pro Ser Glu Ser Lys Asn Ser Pro
         355                 360                 365
Ala Ser Ala Ser Phe His Lys Ala His Glu Glu Gly Leu Gly Ala Gly
 370                 375                 380
Asn Gly Thr Ala Ala Phe Arg Pro Pro Cys Thr Gly Asp Glu Asn Ile
385                 390                 395                 400
Thr Ser Val Glu Thr Pro Tyr Met Asp Phe Thr His Leu Arg Ile Ser
                 405                 410                 415
Tyr Asn Val Tyr Leu Ala Val Tyr Ser Ile Ala His Ala Leu Gln Asp
             420                 425                 430
```

```
Ile Tyr Thr Cys Thr Pro Gly Lys Gly Leu Phe Thr Asn Gly Ser Cys
        435                 440                 445

Ala Asp Ile Lys Lys Val Glu Ala Trp Gln Val Leu Lys His Leu Arg
    450                 455                 460

His Leu Asn Phe Thr Ser Asn Met Gly Glu Gln Val Asp Phe Asp Glu
465                 470                 475                 480

Phe Gly Asp Leu Val Gly Asn Tyr Ser Ile Ile Asn Trp His Leu Ser
                485                 490                 495

Pro Glu Asp Gly Ser Val Val Phe Glu Val Gly His Tyr Asn Val
                500                 505                 510

Tyr Ala Lys Lys Gly Glu Arg Leu Phe Ile Asn Glu Asn Lys Ile Leu
            515                 520                 525

Trp Ser Gly Phe Ser Lys Glu Val Pro Phe Ser Asn Cys Ser Arg Asp
    530                 535                 540

Cys Leu Pro Gly Thr Arg Lys Gly Ile Ile Glu Gly Glu Pro Thr Cys
545                 550                 555                 560

Cys Phe Glu Cys Val Asp Cys Pro Asp Gly Glu Tyr Ser Asp Glu Thr
                565                 570                 575

Asp Ala Ser Ala Cys Asp Lys Cys Pro Glu Asp Tyr Trp Ser Asn Glu
            580                 585                 590

Asn His Thr Ser Cys Ile Pro Lys Gln Ile Glu Phe Leu Ser Trp Thr
        595                 600                 605

Glu Pro Phe Gly Ile Ala Leu Thr Leu Phe Ala Val Leu Gly Ile Phe
    610                 615                 620

Leu Thr Ser Phe Val Leu Gly Val Phe Thr Lys Phe Arg Asn Thr Pro
625                 630                 635                 640

Ile Val Lys Ala Thr Asn Arg Glu Leu Ser Tyr Leu Leu Leu Phe Ser
                645                 650                 655

Leu Leu Cys Cys Phe Ser Ser Ser Leu Phe Phe Ile Gly Glu Pro Gln
            660                 665                 670

Asn Trp Thr Cys Arg Leu Arg Gln Pro Ala Phe Gly Ile Ser Phe Val
        675                 680                 685

Leu Cys Ile Ser Cys Ile Leu Val Lys Thr Asn Arg Val Leu Leu Val
    690                 695                 700

Phe Glu Ala Lys Ile Pro Thr Ser Leu His Arg Lys Trp Trp Gly Leu
705                 710                 715                 720

Asn Leu Gln Phe Leu Leu Val Phe Leu Cys Thr Phe Val Gln Ile Val
                725                 730                 735

Ile Cys Val Ile Trp Leu Tyr Thr Ala Pro Pro Ser Ser Tyr Arg Asn
            740                 745                 750

His Glu Leu Glu Asp Glu Ile Ile Phe Ile Thr Cys His Glu Gly Ser
        755                 760                 765

Leu Met Ala Leu Gly Phe Leu Ile Gly Tyr Thr Cys Leu Leu Ala Ala
    770                 775                 780

Ile Cys Phe Phe Phe Ala Phe Lys Ser Arg Lys Leu Pro Glu Asn Phe
785                 790                 795                 800

Asn Glu Ala Lys Phe Ile Thr Phe Ser Met Leu Ile Phe Phe Ile Val
                805                 810                 815

Trp Ile Ser Phe Ile Pro Ala Tyr Ala Ser Thr Tyr Gly Lys Phe Val
            820                 825                 830

Ser Ala Val Glu Val Ile Ala Ile Leu Ala Ala Ser Phe Gly Leu Leu
        835                 840                 845

Ala Cys Ile Phe Phe Asn Lys Val Tyr Ile Ile Leu Phe Lys Pro Ser
```

```
                   850                 855                 860
Arg Asn Thr Ile Glu Glu Val Arg Cys Ser Thr Ala Ala His Ala Phe
865                 870                 875                 880

Lys Val Ala Ala Arg Ala Thr Leu Arg Arg Ser Asn Val Ser Arg Lys
                885                 890                 895

Arg Ser Asn Ser Leu Gly Gly Ser Thr Gly Ser Thr Pro Ser Ser Ser
                900                 905                 910

Ile Ser Ser Lys Ser Asn His Glu Asp Pro Phe Pro Leu Pro Ala Ser
                915                 920                 925

Ala Glu Arg Gln Arg Gln Gln Gln Arg Gly Cys Lys Gln Lys Val Ser
            930                 935                 940

Phe Gly Ser Gly Thr Val Thr Leu Ser Leu Ser Phe Glu Glu Pro Gln
945                 950                 955                 960

Lys Asn Ala Met Ala Asn Arg Asn Ala Lys Arg Arg Asn Ser Leu Glu
                965                 970                 975

Ala Gln Asn Ser Asp Asp Ser Leu Met Arg His Arg Ala Leu Leu Ala
                980                 985                 990

Leu Gln Asn Ser Glu Ser Leu Ser Ala Glu Pro Gly Phe Gln Thr Ala
            995                 1000                1005

Ser Ser Pro Glu Thr Ser Ser Gln Glu Ser Val Val Gly Asp Asn Lys
        1010                1015                1020

Glu Glu Val Pro Asn Pro Glu Ala Glu Pro Ser Leu Pro Ser Ala Asn
1025                1030                1035                1040

Ser Arg Asn Phe Ile Gly Thr Gly Gly Ser Ser Val Thr Glu Asn Thr
                1045                1050                1055

Val His Ser
```

AVIAN EXTRACELLULAR CALCIUM-SENSING RECEPTOR

CROSS REFERENCE TO RELATED APPLICATIONS

The present application claims the benefit of U.S. provisional application No. 60/058,095, filed on Aug. 18, 1997.

FIELD OF THE INVENTION

The present invention is directed to an avian calcium-sensing receptor protein and to nucleic acid sequences encoding this protein. It encompasses assays that utilize the avian receptor and to transgenic animals that have been engineered to express mutated forms of the receptor. In addition, the invention is directed to methods for altering the activity of calcium receptors by administering small organic polyanions.

BACKGROUND OF THE INVENTION

An extracellular $Ca^{2+}$-sensing receptor (CaR) has been cloned from both bovine and human parathyroids, and there is evidence indicating that this receptor plays a key role in regulating extracellular calcium homeostasis by controlling PTH secretion (Pollak, et al., *Cell* 75:1297–1303 (1993); Pollak, et al., *Nature Genet.* 8:303–307 (1994); Pollak, et al., *J. Clin. Invest.* 93:1108–1112 (1994)). The isolation and identification of the avian counterpart of this receptor and of polynucleotides encoding the receptor should aid in the development of methods for regulating serum calcium levels in chickens and related species. By increasing serum calcium in such animals, it is expected that more rapid growth should be obtainable due to an increased rate of bone deposition and that eggs of higher quality should be produced.

SUMMARY OF THE INVENTION

The present invention is based upon two related discoveries. First, a novel avian extracellular $Ca^{2+}$-sensing receptor has been isolated and characterized. This receptor is structurally distinct from all similar receptors that have been identified and can be used in assays designed to identify agents that lead to an alteration in the serum calcium concentration of birds. Mutated forms of the receptor have been identified that have an altered sensitivity to extracellular calcium. These can be used in the development of transgenic chickens that have a higher than normal concentration of serum calcium and that have improved characteristics in terms of growth and egg production.

The second discovery forming the basis of the present invention is that small organic polyanions can be used to antagonize the interaction of calcium with receptor ("CaR") in chickens and in other species as well. Thus, agents such as suramin may be used to treat patients that are suffering from abnormally low serum calcium concentrations. In addition, these agents may be included in the feed of farm animals (e.g., cattle, pigs, horses, sheep, chickens etc.) to increase the availability of serum calcium for bone deposition. This should lead to animals that are healthier and that grow at a faster rate. In the case of chickens, it should also lead to animals that produce eggs with stronger shells.

In its first aspect, the invention is directed to a substantially pure avian CaR having an amino hacid sequence consisting essentially of the sequence of SEQ ID NO:2 (see also FIGS. 2A–2D). The term "consisting essentially of," is meant to encompass proteins having exactly the same amino acid sequence as that shown in the sequence listing, as well as proteins with differences that are not substantial, as evidenced by their retaining the basic, qualitative functional properties of CaR. A "substantially pure" protein is one that has been separated from other accompanying biological components and will typically comprise at least 85% of a sample, with greater percentages being preferred. Many means are available for assessing the purity of a protein within a sample, including analysis by polyacrylamide gel electrophoresis, chromatography and analytical centrifugation.

The invention encompasses antibodies that bind specifically to avian CaR (i.e., that have at least a hundredfold greater affinity for avian CaR than for any protein that is not an extracellular calcium-sensing receptor) and antibodies made by a process involving the injection of a pharmaceutically acceptable preparation of CaR into an animal capable of antibody production. In a preferred embodiment, monoclonal antibody to avian CaR is produced by injecting the pharmaceutically acceptable preparation into a mouse and then fusing mouse spleen cells with myeloma cells.

The invention is also directed to a substantially pure polynucleotide encoding a protein consisting essentially of the amino acid sequence of SEQ ID NO:2, expression vectors comprising such polynucleotides, and host cells transformed with such vectors. Also included is the recombinant avian CaR receptor protein produced by host cells made in this manner. Preferably, the polynucleotide encoding the avian CaR has the nucleotide sequence of SEQ ID NO:1 (see also FIGS. 2A–2D). It is also preferred that the vectors and host cells prepared for the expression of CaR use this particular polynucleotide.

In another aspect, the present invention is directed to a method for assaying a test compound for its ability to bind to the avian CaR. The method is performed by incubating a source of CaR with a ligand known to bind to the receptor and with the test compound. The CaR used in the assay should be substantially free of other types of $Ca^{2+}$ receptors, i.e., greater than about 90% of the $Ca^{2+}$ receptors present should correspond to CaR. Upon completion of incubation, the ability of the test compound to bind to CaR is determined by the extent to which ligand binding has been displaced. A preferred source of CaR for use in the assay is a cell transformed with a vector for expressing the receptor and comprising a polynucleotide encoding a protein consisting essentially of the amino acid sequence of SEQ ID NO:2. Instead of using cells in the assay, a membrane preparation can be prepared from the cells and this can be used as a source of CaR. Although not essential, the assay can be accompanied by a determination of whether test compounds affect the activity of a second messenger pathway. Preferably this is accomplished either by measuring a product of the activation of phospholipase C (typically inositol phosphate) or by measuring changes in cytosolic calcium levels. Assays of this type should help to determine whether a compound that modulates the activity of CaR is acting as an agonist or antagonist to $Ca^{2+}$.

The invention is also directed to a method for assaying a test compound for its ability to alter the expression of the CaR gene. This method is performed by growing cells expressing CaR, and preferably substantially free of other $Ca^{2+}$ receptors, in the presence of the test compound. Cells are then collected and the expression of CaR is compared with expression in control cells grown under essentially identical conditions but in the absence of the test compound. In preferred embodiments, the cells expressing CaR are cells transformed with an expression vector comprising a polynucleotide sequence encoding a protein consisting essentially of the amino acid sequence of SEQ ID NO:2. Test compounds that may be used include oligonucleotides at least 15 nucleotides in length and comprising a sequence complementary to a sequence shown in SEQ ID NO:1. The preferred method for determining receptor expression is by means of Western blot analysis using CaR-specific antibody.

In another aspect, the present invention is directed to a DNA construct that can be used in the development of transgenic animals expressing a mutated form of CaR. The construct should contain a targeting segment that consists essentially of the nucleotide sequence encoding the wild type avian CaR gene, as shown SEQ ID NO:2, but in which one or more nucleotides in codon 127 have been modified. It has been found that mutations in this codon result in receptors that have an altered sensitivity to $Ca^{2+}$. Preferred mutations for reducing the sensitivity of CaR to extracellular calcium are those that result in codon 127 encoding tryptophan. Preferred mutations for increasing the sensitivity of CaR to extracellular calcium are those that result in codon 127 encoding lysine, asparagine, valine, glutamine, and alanine. The targeting segment encoding the mutated form of CaR is operably linked to a promoter that is active in avian cells. The invention encompasses transgenic animals, e.g., chickens, that have incorporated such a targeting segment into their genome.

The invention is also directed to a method for producing a transgenic chicken that expresses a form of CaR that has undergone a mutation at codon 127 (preferably resulting in the codon encoding tryptophan, lysine, asparagine, valine, glutamine or alanine). The first step in this method involves making a DNA construct according to the procedures set forth above and introducing this construct into the genome of a retrovirus, preferably an avian leukosis virus. Viruses engineered in this manner are injected near the blastoderm of fertile chicken eggs which are then incubated until they hatch. The chicks thus produced are screened to determine whether they are expressing the mutated form of CaR. Initially, screening may be performed by assaying the serum of the chickens to determine if the levels of calcium or PTH are abnormally elevated or decreased. Alternatively DNA may be obtained from the blood or tissues of the chickens and analyzed to determine if it contains a segment encoding mutated CaR. Analysis can be performed by Southern hybridization using a labeled probe which binds to the DNA segment encoding the mutated CaR. Transgenic animals produced by this method are included as part of the invention.

In related work, it has been discovered that small organic polyanions are capable of antagonizing the effect of calcium on CaR. Based upon this discovery, a method has been developed for treating a patient for a condition caused by a low concentration of serum calcium. The method involves administering to the patient a small organic polyanion at a dosage and for a duration sufficient to significantly increase the level of serum calcium. In this context, a "significant" increase is one determined to be significant using standard statistical analyses, e.g., $p<0.05$. Preferably, the small organic polyanion administered to a patient is suramin.

Alternatively, a small organic polyanion, preferably suramin, may be included in the feed of animals (e.g. cattle, horses, pigs, sheep, chickens etc.) to increase serum levels of calcium. The feed is administered to an animal and, by increasing serum calcium levels, should lead to an improvement in health and rate of growth. The invention encompasses not only the procedure, but also the feed that has been supplemented with the small organic polyanion and, more specifically, feed supplemented with suramin.

BRIEF DESCRIPTION OF THE FIGURES

FIGS. 1a–1c: Expression of transcripts for the chicken CaR in parathyroid gland as assessed by Northern analysis: (1a) Northern analysis on poly(A+) RNA obtained from a vitamin D-deficient chicken. Samples of 5 µg poly(A+) RNA were hybridized with a randomly primed, $^{32}$P-labeled bovine CaR probe. The size of the single hybridizing band is indicated in the margin. (1b) In situ hybridization of parathyroid tissue with a 5' antisense digoxigenin-labeled chicken CaR riboprobe. (1c) In situ hybridization using a 5' sense digoxigenin-labeled chicken CaR riboprobe in fixed parathyroid tissue as in (1b).

FIGS. 2(A)–2(D): Nucleotide and deduced amino acid sequences of the chicken CaR clone C1D: Both strands of the C1D clone were sequenced using the dideoxy chain termination method. Analyses of nucleotide and deduced amino acid sequences were carried out as described under Examples. Nucleotides are numbered from the beginning of the clone. The corresponding amino acids are shown in single letter code.

FIGS. 4(A)–4(B): Alignment of amino acid sequences of chicken and human CaR: The sequences for the chicken and human CaRs are aligned with identities enclosed in boxes. Similarities and differences in amino acid sequence are discussed in the Examples section.

DEFINITIONS

Figure 3:
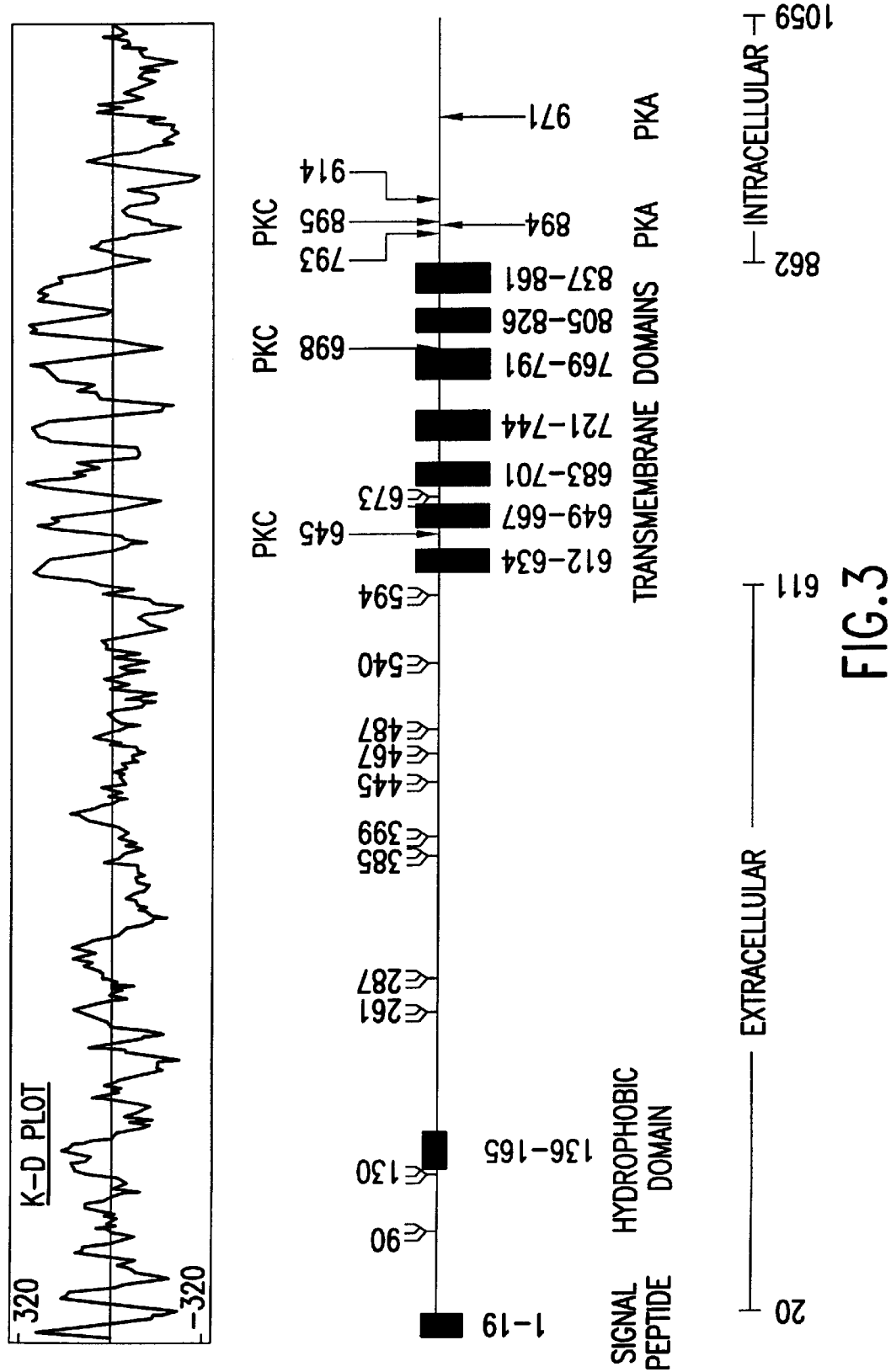
FIG. 3: Hydropathy analysis and structural features of the chicken CaR predicted by amino acid sequence: The upper panel shows the hydropathy plot as a function of the amino acid position using a window of 10, with positive values indicating hydrophobic regions and negative values representing hydrophilic regions. The lower panel provides a schematic representation of the main structural features of the predicted chicken CaR protein. Potential sites for N-glycosylation, protein kinase C and protein kinase A phosphorylation are indicated. Shaded areas illustrate specific domains.

The description that follows uses a number of terms that refer to recombinant DNA technology. In order to provide a clear and consistent understanding of the specification and claims, the following definitions are provided.

Expression vector: A vector which is capable of inducing the expression of DNA that has been cloned into it after transformation into a host. The cloned DNA is usually placed under the control of (i.e., operably linked to) regulatory sequences such as promoters or enhancers. Promoter sequences may be constitutive, inducible or repressible.

Host: Any prokaryotic or eukaryotic cell that is the recipient of an expression vector is the "host" for that vector. The term encompasses cells that have been engineered to incorporate a desired gene into their chromosome or genome. Examples of cells that can serve as hosts are well known in the art, as are techniques for cellular transformation (see e.g., Sambrook, et al., *Molecular Cloning: A Laboratory Manual,* 2nd ed., Cold Spring Harbor (1989)).

Promoter: A DNA sequence, typically found in the 5' region of a gene, located proximal to the start codon. Transcription is initiated at the promoter. If the promoter is of the inducible type, then the rate of transcription increases in response to an inducing agent.

Operably linked: The term "operably linked" refers to genetic elements that are joined in such a manner that enables them to carry out their normal functions. For example, a gene is operably linked to a promoter when its transcription is under the control of the promoter and such transcription produces the protein normally encoded by the gene.

DETAILED DESCRIPTION OF THE INVENTION

The present invention is directed to the avian CaR protein, genetic sequences coding for the receptor, a method for assaying compounds to determine their ability to modulate the activity of CaR, a method for assaying compounds for their ability to alter CaR expression, to transgenic animals produced using mutated forms of CaR, and, finally, to more generalized methods for regulating the serum concentration of calcium using small organic polyanions.

The avian form of CaR may be distinguished from all similar receptors previously disclosed based upon its structure. In this regard, it will be understood that the present invention encompasses not only amino acid and nucleotide sequences identical to those of SEQ ID NO:2, but also sequences that are essentially the same and sequences that are otherwise substantially the same and which result in a receptor retaining the basic binding characteristics of CaR. For example, it is well known that techniques such as site-directed mutagenesis may be used to introduce variations into a protein's structure. Variations in CaR introduced by this or some similar method are encompassed by the invention, provided that the resulting receptor retains the ability to respond to extracellular $Ca^{2+}$.

I. Nucleic Acid Sequences Coding for Avian CaR

DNA sequences coding for avian CaR are present in a variety of tissues, any of which may serve as a source for the isolation of nucleic acid coding for the receptor. In chickens, the preferred source is parathyroid tissue, but other tissues such as the kidney and brain can also be used. In addition, cells and cell lines that express CaR may serve as a source for nucleic acid. These may either be cultured cells that have not undergone transformation or cell lines specifically engineered to express recombinant CaR.

Many methods are available for isolating DNA sequences and may be adapted for the isolation of CaR nucleic acid (see, e.g., Sambrook, et al., supra). One preferred method is to screen a cDNA library prepared from chicken parathyroid mRNA using a probe complementary to a known sequence in CaR. One probe that has been found successful in this regard is described in the Examples section and consists of an 816 base pair fragment corresponding to nucleotides 341–1157 of bovine parathyroid CaR (Brown, et al., *Cell* 83:679–682 (1995)). The methodology used for screening cDNA libraries is well known in the art and a specific example is provided in Example 1.

Although the bovine probe discussed above has been found to be suitable for screening cDNA libraries for avian CaR, it is expected that a wide variety of other probes can be used equally well. For example, cDNA libraries may be screened using probes synthesized based upon the avian CaR sequence shown in FIG. 2. In general, probes should be at least 14 nucleotides long and should not be selected from regions known to be highly conserved among proteins, e.g., the transmembrane domains of G-protein linked receptors. One way to easily produce a large amount of probe is to use the polymerase chain reaction (PCR) to amplify the desired sequence from a cDNA library. For example, PCR may be performed on a cDNA library using primers to flank the sequence desired as a probe. Amplified fragments can be size fractionated on an agarose gel and the selected fragments inserted into an appropriate vector. Alternatively, probes may be synthesized using well established methods.

The above procedure is known to be suitable for obtaining avian CaR nucleic acid, however, it is expected that alternative techniques can be developed with relatively little effort. For example, using the sequences shown in the figure, it should be possible to select PCR primers that amplify the full-length CaR sequence.

II. Production and Isolation of CaR Recombinant Protein

In order to express recombinant avian CaR, the DNA sequence encoding the protein must be placed in a vector containing transcriptional and translational signals recognizable by an appropriate host. The cloned CaR sequences, preferably in double-stranded form, are inserted into the expression vector in an operable linkage, i.e., they are positioned so as to be under the control of the vector's regulatory sequences and in such a manner that mRNA is produced which is translated into CaR.

Expression of CaR protein in different hosts may result in different post-translational modifications that can, potentially, alter the properties of the receptor. Mammalian cells that may be used include, without limitation, NIH-3T3 cells, CHO cells, HeLa cells, and LM(tk–) cells, etc. Vectors suitable for use in each of these various cell types are well known in the art (see, e.g., Sambrook, et al., supra). Preferred eukaryotic promoters include that of the mouse metallothionein gene, the TK promoter of Herpes virus, the SV40 early promoter, and the yeast GAL4 gene promoter.

Expression vectors may be introduced into host cells by methods such as calcium phosphate precipitation, microinjection, electroporation or viral transfer. Cells expressing CaR can be selected using methods well known in the art. One simple method for confirming the presence of the receptor nucleic acid in cells is to perform PCR amplification using primers known to flank the CaR sequence. The presence of functional receptor may be confirmed by performing binding assays using labeled $Ca^{2+}$.

Once cells producing recombinant CaR have been identified, they may be used in binding says, assays designed to identify agents capable of altering CaR expression, or in assays measuring CaR activity by determining levels of cytosolic calcium or inositol phosphate.

III. Antibodies to CaR

The present invention encompasses antibodies that bind specifically to avian CaR and the process for producing such antibodies. Antibodies that "bind specifically to CaR" are defined as those that have at least a hundredfold greater affinity for CaR than for any unrelated protein, i.e., any protein that is not an extracellular calcium-sensing receptor. The process for producing such antibodies may involve either injecting the CaR protein itself into an appropriate animal or, alternatively, injecting short peptides made to correspond to different regions of CaR. The peptides should be at least five amino acids in length and should be selected from regions believed to be unique to CaR.

Methods for making and selecting antibodies are well known to those of skill in the art, as evidenced by standard reference works such as: Harlow, et al., *Antibodies, A Laboratory Manual*, Cold Spring Harbor Laboratory N.Y. (1988); Klein, *Immunology: The Science of Self-Nonself Discrimination* (1982); Kennett, et al., *Monoclonal Antibodies and Hybridomas: A New Dimension in Biological Analyses* (1980); and Campbell, "Monoclonal Antibody Technology" in laboratory techniques in biochemistry and molecular biology.

"Antibody" as used herein is meant to include intact molecules as well as fragments which retain their ability to bind to antigen (e.g., Fab and F(ab')$_2$ fragments). The term "antibody" also refers to both monoclonal antibodies and polyclonal antibodies. Polyclonal antibodies are derived from the sera of animals immunized with antigen. Monoclonal antibodies can be prepared using hybridoma technology (Kohler, et al., *Nature* 256:495 (1975); Hammerling, et al., In: Monoclonal Antibodies and T-Cell Hybridomas, Elsevier, N.Y. pp. 563–681 (1981)). In general, this technology involves immunizing an animal, usually a mouse, with either intact CaR or a fragment derived from CaR. The splenocytes of the immunized animals are extracted and fused with suitable myeloma cells, e.g., $SP_2O$ cells. After fusion, the resulting hybridoma cells are selectively maintained in HAT medium and then cloned by limiting dilution (Wands, et al., *Gastroenterology* 80:225–232 (1981)). The cells obtained through such selection are then assayed to identify clones which secrete antibodies capable of binding to CaR.

The antibodies, or fragments of antibodies, of the present invention may be used to detect the presence of CaR protein using any of a variety of immunoassays. For example, the antibodies may be used in radioimmunoassays or in immunometric assays, also known as "two-site" or "sandwich" assays (see Chard, "An Introduction to Radioimmune Assay and Related Techniques," in: Laboratory Techniques in Biochemistry and Molecular Biology, North Holland Publishing Co., N.Y. (1978)). In a typical immunometric assay, a quantity of unlabeled antibody is bound to a solid support that is insoluble in the fluid being tested, e.g., blood, lymph, cellular extracts, etc. After the initial binding of antigen to immobilized antibody, a quantity of detectably labeled second antibody (which may or may not be the same as the first) is added to permit detection and/or quantitation of bound antigen (see, e.g., Radioimmune Assay Method, Kirkham, et al., ed. pp. 199–206, E&S Livingstone, Edinburgh (1970)). Many variations of these types of assays are known in the art and may be employed for the detection of CaR.

Antibodies to CaR may also be used in the purification of either the intact receptor or fragments of the receptor (see generally Dean, et al., Affinity Chromatography, A Practical Approach, IRL Press (1986)). Typically, antibody is immobilized on a chromatographic matrix such as Sepharose 4B. The matrix is then packed into a column and the preparation containing CaR is passed through under conditions that promote binding, e.g., under conditions of low salt.

The column is then washed and bound CaR is eluted using a buffer that promotes dissociation from antibody, e.g., buffer having an altered pH or salt concentration. The eluted CaR may be transferred into a buffer of choice, e.g., by dialysis, and either stored or used directly.

IV. Assay for Compounds That Alter CaR Activity

One of the main uses for CaR nucleic acids and recombinant proteins is in assays designed to identify agents capable of binding to CaR receptors or which measure a secondary effect of calcium/receptor interaction. Such agents may either be agonists, mimicking the effects of calcium, or antagonists, inhibiting the effects of calcium. Of particular interest is the identification of agents which lead to an increase in serum levels of calcium. Such agents could be used in chickens to elevate calcium levels to produce eggs of better quality, i.e., having a sturdier shell and therefore less likely to break. Provided the agents are pharmaceutically acceptable, they could also be used to treat patients with disorders characterized by low levels of calcium.

The essential feature of binding assays is that a source of CaR is incubated together with a ligand known to bind to the receptor and with a compound being tested for binding activity. The preferred source for CaR is cells transformed to recombinantly express the receptor. The cells selected should not express a substantial amount of other receptors which interact with calcium. This can easily be determined by performing calcium binding assays on cells derived from the same tissue or cell line as those recombinantly expressing CaR but which have not undergone transformation.

The assay may be performed either with intact cells or, alternatively, with membranes prepared from the cells (see, e.g., Wang, et al., *Proc. Nat'l Acad. Sci. USA* 90:1023–10234 (1993)). The membranes are incubated with a ligand that binds to CaR and with a preparation of the compound being tested. After binding is complete, receptor is separated from the solution containing ligand and test compound, e.g., by filtration, and the amount of binding that has occurred is determined. Nonspecific binding may be determined by carrying out the binding reaction in the presence of a large excess of unlabeled ligand. For example, detectable ligand may be incubated with receptor and test compound in the presence of a thousandfold excess of unlabeled ligand. Nonspecific binding should be subtracted from total binding, i.e., binding in the absence of unlabeled ligand, to arrive at the specific binding for each sample tested. Other steps such as washing, stirring, shaking, filtering and the like may be included in the assays as necessary. Typically, wash steps are included after the separation of membrane-bound ligand from ligand remaining in solution and prior to the quantitation of the amount of ligand bound, e.g., by counting radioactive isotope. The specific binding obtained in the presence of test compound is compared with that obtained in the presence of labeled ligand alone to determine the extent to which test compound has displaced ligand.

In performing binding assays, care must be taken to avoid artifacts which may make it appear that a test compound is binding to CaR when, in fact, binding is being inhibited by some other mechanism. For example, the compound being tested should be in a buffer which does not itself substantially inhibit the binding of ligand to receptor and should, preferably, be tested at several different concentrations. It is highly desirable that compounds identified as displacing the binding of ligand to CaR be reexamined in a concentration range sufficient to perform a Scatchard analysis on the results. This type of analysis is well known in the art and can be used for determining the affinity of a test compound for receptor (see, e.g., Ausubel, et al., Current Protocols in Molecular Biology, 11.2.1–11.2.19 (1993); Laboratory Techniques in Biochemistry and Molecular Biology, Work, et al., ed., N.Y. (1978)). Computer programs may be used to help in the analysis of results (see, e.g., Munson, *Methods Enzymol.* 92:543–577 (1983); McPherson, Kinetic, EBDA Ligand, Lowry—A Collection of Radioligand Binding Analysis Programs, Elsevier-Biosoft, U.K. (1985)).

As an alternative, assays may be performed to determine whether a test compound alters the responsiveness of cells to extracellular calcium. Typically such assays involve measuring changes in cytosolic calcium or the generation of inositol phosphate in response to changes in extracellular calcium. A description of the basic measurement techniques appears in Example 2 below. Preferably test compounds will be examined at several concentrations both in the presence and absence of extracelluar calcium.

V. Agents That Act as CaR Antagonists

It has been discovered that there are two general classes of compounds that function as CaR antagonists. The first class is made up of inorganic salts such as sodium chloride, sodium sulfate or sodium gluconate. The second class of compounds is made up of small organic polyanions, such as suramin.

Suramin, or a similar polyanion, may be orally administered to patients in order to raise their serum calcium concentration. Physicians may begin by administering relatively small doses of polyanion and then adjust the dosage upward as it becomes clear that the patient can tolerate the treatment. For example, a physician may begin by administering 1 nmol/kg/day and increase the dosage to 1 μmol/kg/day, using blood calcium concentration as a guide. The final dosage may be provided in either a single or multiple regimen with the latter being generally preferred. These are simply guidelines since the actual dose must be carefully selected and titrated by the attending physician based upon clinical factors unique to each patient. The optimal daily dose will be determined by methods known in the art and will be influenced by factors such as the age of the patient, disease state, side effects associated with the particular agent being administered and other clinically relevant factors. In many cases, a patient will already be taking medications at the time treatment with the polyanion is initiated. These other medications may be continued during the time that polyanion is administered to the patient but it is particularly advisable in such cases to begin with low doses to determine if adverse side effects are experienced.

Alternatively, suramin, or a similar polyanion, may be incorporated into the feed of animals as a means for increasing their serum calcium concentration. This should lead to animals with improved growth characteristics and, in the case of chickens, such administration should improve egg production characteristics. The exact concentration to be used in the feed can be empirically determined by gradually increasing the concentration while measuring a desired characteristic, i.e., the rate of growth. Once further addition of agent does not result in a corresponding increase in the desired characteristic, the optimal concentration has been found and no further increases should be made.

VI. Assay for Ability to Modulate CaR Expression

One way to either increase or decrease serum calcium levels in a subject is to alter the extent to which CaR is expressed in cells. Therefore, assays for the identification of compounds that either inhibit or enhance expression are of considerable interest. These assays are carried out by growing cells expressing CaR in the presence of a test compound and then comparing receptor expression in these cells with cells grown under essentially identical conditions but in the absence of the test compound. Expression can be followed either directly, e.g., using Western blots, or indirectly, e.g., by measuring the responsiveness of cells to extracellular concentrations of calcium using changes in cytosolic calcium or inositol phosphate as a benchmark. One group of test compounds that may be included for modulating CaR expression consists of oligonucleotides complementary to various segments of the CaR sequence. These oligonucleotides should be at least 15 bases in length and should be derived from non-conserved regions of the receptor nucleic acid sequence.

Oligonucleotides which are found to reduce or enhance receptor expression may be derivatized or conjugated in order to increase their effectiveness. For example, nucleoside phosphorothioates may be substituted for their natural counterparts (see Cohen, Oligodeoxynucleotides, Antisense Inhibitors of Gene Expression, CRC Press (1989)). The oligonucleotides may be delivered to a subject in vivo for the purpose of inhibiting CaR expression. When this is done, it is preferred that the oligonucleotide be administered in a form that enhances its uptake by cells. For example, the oligonucleotide may be delivered by means of a liposome, retrovirus, or conjugated to a peptide that is ingested by cells (see, e.g., U.S. Pat. Nos. 4,897,355 and 4,394,448). Other methods for enhancing the efficiency of oligonucleotide delivery are well known in the art and are also compatible with the present invention.

VII. Production of Transgenic Animals With Mutated Forms of CaR

Figure 9:
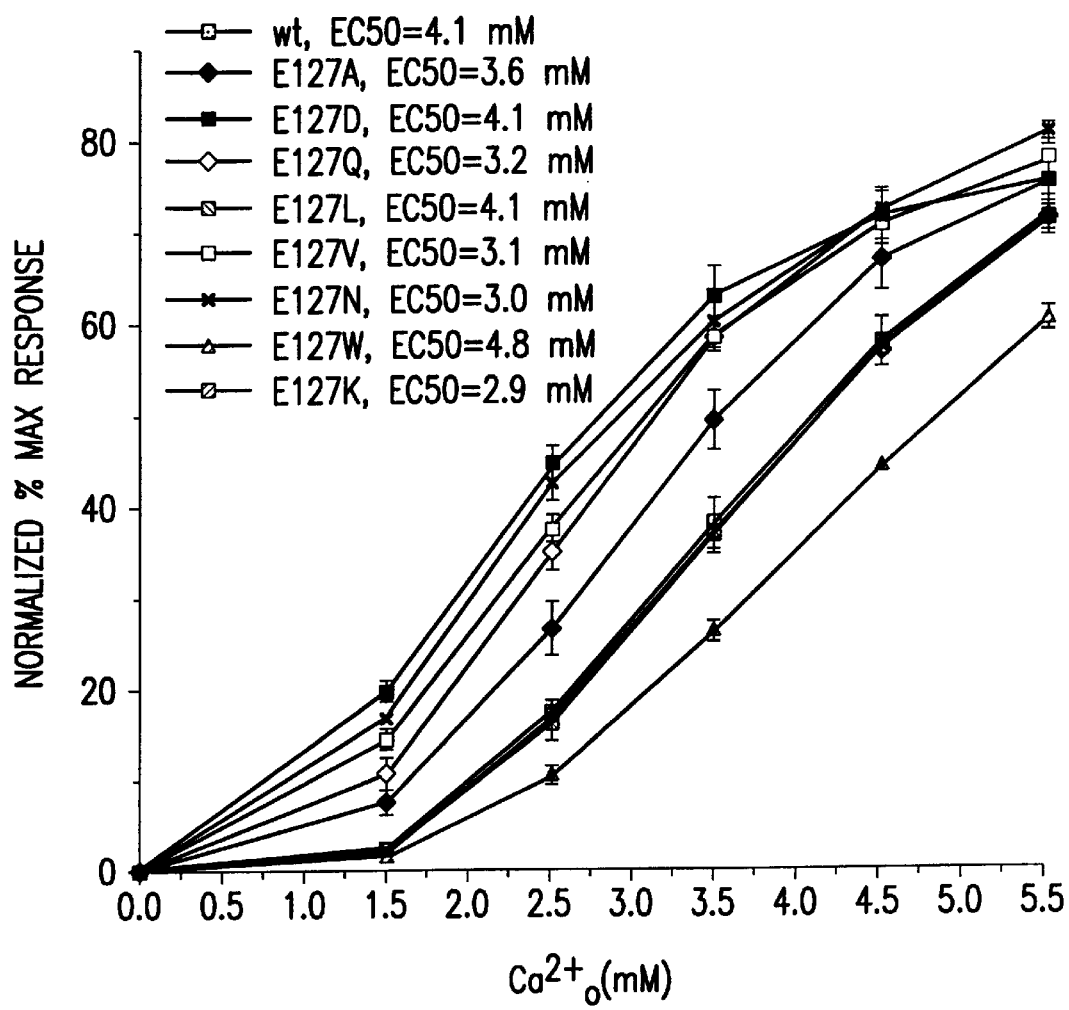
FIG. 9: Effect of Mutations at Codon 127 on Receptor Sensitivity: Mutations at position 127 in the CaR protein were found to alter the sensitivity of the receptor to extracellular calcium. The figure shows the responsiveness of receptors mutated so that position 127 is occupied by alanine, aspartate, glutamine, leucine, valine, asparagine, tryptophan and lysine. The curve for the wild type receptor (wt) is also shown and the $EC_{50}$ for each receptor tested is listed.

It has been found that mutations to codon 127 of the CaR nucleic acid sequence produce a receptor with an altered sensitivity to calcium(see FIG. 9). Mutations resulting in codon 127 encoding tryptophan result in a receptor with reduced sensitivity, whereas mutations resulting in codon 127 encoding lysine, asparagine, valine, glutamine or alanine produce a receptor with an increased sensitivity. The mutated forms of CaR may be operably linked to a promoter and used as part of a larger construct in the production of transgenic animals, preferably chickens. A number of articles have been written describing the way in which transgenic chickens may be produced (Salter, et al., *Virology* 157:236–240 (1987); Love, et al., *Bio/Technology* 12:60–63 (1994); Crittendon, et al., *J. Reprod. Fert. Suppl.* 41:163–171 (1990); Carsience, et al., *Development* 117:669–675 (1993)). The preferred method for making transgenic chickens is to incorporate DNA constructs into the genome of avian leukosis viruses and then inject the viruses near the blastoderm of fertile eggs prior to incubation. The embryo of a newly laid fertile egg is pluripotent and the injection of avian leukosis viruses near the embryo serves to infect some germ cells.

After eggs are hatched, chicks may be screened for the incorporation of mutant CaR. The easiest way to perform an initial screening is to test the serum of the hatched chickens to determine the concentration of calcium. Depending on the specific mutation utilized, a transgenic chicken should evidence either a substantial increase or reduction in the normal amount of calcium found in the blood. Similarly, PTH levels in the chicken serum can be assayed.

An alternative way to screen is by extracting DNA from the blood or tissues of the chickens using standard procedures (see Sambrook, et al., supra). The DNA may then be digested using restriction enzymes, electrophoresed and transferred to a nylon membrane. The immobilized DNA may then be hybridized under conditions of high stringency to a $^{32}$P-labeled probe corresponding to the mutated CaR DNA (see generally Jenkins, et al., *Cell* 43:811–819 (1985)). Autoradiography of the hybridized nylon membranes should reveal whether a particular chicken has DNA encoding mutant CaR. Alternatively, DNA may be amplified using PCR in conjunction with primers flanking a region of the CaR DNA. By carefully selecting primers, only those chickens that have incorporated mutant CaR DNA should produce an amplification product.

Methods for the development of transgenic animals in other species, particularly the mouse have been established and can readily be adapted to the making of animals expressing avian CaR and mutated forms of avian CaR (see, Mansour, et al., *Nature* 336:348 (1988); Capecchi, *TIG* 5:70 (1989); Bradley, et al., *Nature* 309:255 (1984); Thomas, et al., *Cell* 51:503 (1987); and Doetschman, et al., *Nature* 330:576 (1987); Robertson, *In Teratocarcinomas and Embryonic Stem Cells: A Practical Approach*, E. J. Robertson, ed, IRL Press, Washington, D.C. (1987); Bradley, et al., *Current Topics in Devel. Biol.* 20:357–371 (1986); and Hogan, et al., *Manipulating the Mouse Embryo: A Laboratory Manual*, Cold Spring Harbor Laboratory Press, Cold Spring Harbor, N.Y. (1986)).

EXAMPLES

Example 1

Cloning, Expression and Characterization of the Avian Calcium-Sensing Receptor Materials and Methods Birds. For cloning and in situ hybridization of the CaR in parathyroid gland, hyperplastic glands were obtained from vitamin D-deficient chickens. Day-old broiler chickens (Cobbs) were obtained from a commercial hatchery and immediately fed a vitamin D-deficient diet containing (g/kg): sorghum grain, 587; soybean oil meal, 35; soybean oil, 2; dicalcium phosphate, 22; calcium carbonate, 12; D,L-methionine, 2.3; choline chloride, 0.4; sodium chloride, 3; vitamin D-free vitamin mix, 2; trace mineral mixture, 1. Hyperplastic glands were harvested from the chickens at the fourth week on this vitamin D-deficient diet. For Northern analysis, samples of kidney, brain and duodenum were taken from a 6-month old Leghorn bird raised on a complete diet and from a day-old Cobb male broiler chicken.

mRNA preparation. Parathyroid glands were dissected out of the neck region of chickens and immediately frozen in liquid nitrogen. Total cellular RNA was isolated from the tissue using either TRIzol (Gibco-BRL Life Technologies, Inc., Gaithersburg, Md.), according to the manufacturer's instructions, or homogenization with guanidinium thiocyanate followed by sedimentation through CsCl, as described previously (Brown et al., *Nature* 366:575–580 (1993); Chattopadhyay, et al., *Am. J. Physiol.* 271 (Renal Fluid Electrolyte Physiol. 40):F736–F743 (1996); Pollak et al., *Cell* 75:1297–1303 (1993)). Poly(A$^+$) RNA was purified by a single passage over an oligo(dT)-cellulose column (type 7, Pharmacia-LKB Biotechnology Inc., Piscataway, N.J.) as described previously (Chattopadhyay, et al., *Am. J. Physiol.* 271 (Renal Fluid Electrolyte Physiol. 40):F736–F743 (1996)).

Northern blot analysis. Aliquots of 5 µg poly(A$^+$) RNA were separated on 2.2 M formaldehyde-1% agarose gels. The RNA was then transferred onto nylon membranes (Duralon, Stratagene, LaJolla, Calif.). Membranes were prehybridized for 2 hours at 42° C. in 40% formamide, 50% dextran sulfate, 3×Denhardt's solution (50×Denhardt's=5 g Ficoll, 5 g polyvinyl-pyrrolidone, and 5 g BSA), 5×standard saline citrate (SSC) (20×SSC=3 M NaCl, 0.3 M Na$_3$-citrate-2H$_2$O), 0.5% sodium dodecyl sulfate (SDS), 7 mM Tris-HCl (pH 7.5), 250 µg/ml yeast tRNA and 200 µg/ml calf thymus DNA, following standard procedures (Ruat, et al., *J. Biol. Chem.* 271:5972–5975 (1996)). Hybridization was carried out overnight at 42° C. in the same solution but after addition of either random-primed cDNA or antisense RNA probes. Following hybridization, the nylon membranes were washed twice with 2×SSC and 0.2% SDS for 20 min at room temperature, followed by a wash with 2×SSC and 0.2% SDS at 65° C. for 15 min and two washes with 0.1×SSC and 0.2% SDS at 65° C. for 15 min. Washing at high stringency (when the chicken specific riboprobe was used) was carried out in 0.1×SSC and 0.1% SDS at 65° C. for 20–40 minutes. The membranes were subsequently stripped and rehybridized using a probe for β-actin mRNA to normalize the amount of RNA loaded in each lane.

Probes. The bovine CaR cDNA probe was an 816 base pair (bp), Pvu II-Spe I fragment corresponding to nucleotides (nt) 341–1157 of the bovine parathyroid CaR cDNA (Brown, et al., *Cell* 83:679–682 (1995)). Probes were labeled by random priming with $^{32}$P-dCTP using a random hexamer priming kit (T7, Quickprime Pharmacia, Piscataway, N.J.). The chicken CaR probe originated from the C1D clone described below in Results. A 1.4 kilobase (kb) fragment of this clone, corresponding to nt 1–1422 and which includes the 5' end of the open reading frame, was sucloned into the pBlueScript II(SK$^+$) vector (Stratagene, La Jolla, Calif.). For riboprobe labeling, the plasmid was linearized with Kpn I. The probes were labeled using T$_3$ RNA polymerase and $^{32}$P-UTP (TransProbe T kit, Pharmacia, Piscataway, N.J.) or digoxigenin-UTP (Boeringer-Mannheim, GMBH). DNA probes of the chicken CaR sequence were labeled by random priming using the same 1.4 kb fragment described above.

Cloning of the cDNA coding for the chicken Ca$^{2+}_o$-sensing receptor. A cDNA library was constructed from chicken parathyroid mRNA using the SuperScript II Lambda system (Gibco-BRL Life Technologies, Inc., Gaithersburg, Md.). cDNA was synthesized according to the manufacturer's recommended procedures. After Not I digestion of the linkers, the cDNA library was size-selected from 3 to 23 kb and ligated into the lambda gt22A vector predigested with Not I and Sal I. For packaging, the Stratagene kit (Gigapack II Gold Packaging, Stratagene, LaJolla, Calif.) was employed. The phage were then introduced into *E. coli* Y1090 (r–). About 250,000 clones were plated at a density of 25,000 plaques/plate on LB agar plates containing 100 µg/ml of ampicillin. Plaques were lifted onto nitrocellulose filters and screened by hybridization using the bovine CaR cDNA probe. Conditions for the primary and secondary screens were as described for Northern blot analysis. Washing of the filters was carried out in 2×SSC, 0.1% SDS at room temperature for 5 min, followed by two washes at 55° C. for 30 minutes and two washes with 0.1×SSC, 0.1% SDS at 55° C. for 30 minutes.

Nucleotide sequencing. Bi-directional sequencing was performed by the dideoxy chain termination method (Brown, et al., *Nature* 366:575–580 (1993); Riccardi, et al. *Proc. Nat'l Acad. Sci. USA* 92:131–135 (1995)) using an Applied Biosystems model 373A automated sequencer (Department of Genetics, Children's Hospital, Boston, Mass.). GeneWorks software version 2.3.1 (IntelliGenetics, Mountain View, Calif.) was utilized for nucleotide and amino acids analyses.

Immunohistochemistry of chicken kidney: For immunohistochemistry, a modification of the method previously described (Kifor, et al., *J. Clin. Endocrinol. Metab.* 81:1598–1606 (1996); Mithal, et al., *Endocrinology* 136:3087–3092 (1995)) was used. Frozen sections from chicken kidney (4 µm) were prepared with a cryostat (–20° C.) and fixed in acetone for 10 min at the same temperature. After air-drying, endogenous peroxidase activity was inhibited by incubating the sections in DAKO Peroxidase Blocking Reagent (Dako Corp., Carpenteria, Calif.) for 10 min followed by treatment with DAKO Protein Block Serum-free solution for 1 hour. The sections were then incubated overnight at 4° C. with 5 µg/ml of a mouse monoclonal antibody directed against a peptide within the extracellular domain of the human CaR (ADD; generously provided by Drs. Allen M. Spiegel and Paul Goldsmith, NIDDK, NIH, Bethesda, Md.), with or without preincubation with the synthetic human CaR peptide against which the antibody was raised (amino acids 214–236, which are identical in human and chicken CaRs). After washing the sections three times with 0.5% BSA in phosphate-buffered saline (PBS) for 20 min each, peroxidase-coupled, goat anti-mouse secondary antiserum (Sigma, St. Louis, Mo.) was added at a dilution of 1:200. After 1 hour incubation at room temperature, sections were washed three times with PBS for 20 minutes each. Color was developed using the DAKO AEC Substrate System for about 5 min. The reaction was stopped by washing three times in water. Some kidney sections were stained with hematoxylin for 2 minutes and mounted in Aqua-Mount (Lerner Laboratories, Pittsburgh, Pa.). Photomicrographs were taken at a magnification of 400×. Staining with antiserum was specific as assessed by its total abolition following preabsorption with specific peptide. In addition, this antiserum shows CaR-specific bands on Western analysis, similar to those we have characterized previously with polyclonal anti-CaR antiserum (Bai, et al., J. Biol. Chem. 271:19537–19545 (1996)).

In situ hybridization. Parathyroid glands were collected from the vitamin D-deficient chickens into PBS solution and fixed overnight in 4% paraformaldehyde in PBS at 4° C. Serial 5 μm sections were prepared after the samples had been dehydrated in a graded series of ethanol solutions, cleared in chloroform and embedded in Paraplast. For hybridization, the sections were deparafinized in xylene, rehydrated through a series of graded ethanol solutions, rinsed in distilled water (5 min), and incubated in 2×SSC at 70° C. for 30 minutes. The sections were then rinsed in distilled water and treated with pronase (0.125 mg/ml in 50 mM Tris-HCl, 5mM EDTA, pH 7.5) for 10 min. After digestion, slides were rinsed with distilled water, postfixed in 10% formaldehyde in PBS, blocked in 0.2% glycine, rinsed in distilled water, rapidly dehydrated through a series of ethanol solutions, and air-dried for several hours. The sections were hybridized with the same probe used for tissue screening that was transcribed in both the sense and antisense directions using $T_7$ and $T_3$ RNA polymerase, respectively. Transcription was carried out in the presence of digoxigenin-UTP (Pines, et al., Matrix Biol. 14:765–771 (1995)).

Expression of the chicken CaR in Xenopus laevis oocytes. The assay is based on injection of synthetic RNA (cRNA) for the chicken CaR into Xenopus oocytes and measurement of agonist-dependent inward currents due to CaR-mediated stimulation of $Ca^{2+}$-activated $Cl^-$ channels (Brown, et al., Nature 366: 575–580 (1993)). In preparing, handling and injecting the oocytes, the techniques of Hediger et al. were followed (Proc. Nat'l Acad. Sci. USA 84:2634–2637 (1987)). cRNA was transcribed from the C1D one as previously described (Brown et al. Nature 336:575–580 (1993)). In vitro transcription of cRNA was done with T7 RNA polymerase in the presence of a cap analog ($m^7$-GpppG, Pharmacia Biotech, Upsala, Sweden). Defolliculated oocytes were injected with 50 nl of a 0.25 μg/μl aqueous solution of CaR cRNA or with the same volume of $H_2O$ as a negative control. The injected oocytes were then incubated in ND96 "standard" solution containing 92 mM Na, 5 mM K, 0.5 mM $CaCl_2$ 0.5 mM MgCl and 5 mM Hepes, pH 7.5, for 3–4 days before electrophysiological study. $Cl^-$ currents were elicited by treatment of the oocytes with increasing concentrations of $Ca^{2+}_0$, $Mg^{2+}_0$ or $Gd^{3+}_0$ and were measured using two electrode voltage clamp at a holding potential of −50 mM, as described in detail previously (Brown et al. Nature 336:575–580 (1993); Riccardi, et al. Proc. Nat'l Acad. Sci. USA 92:131–135 (1995)).

Results

Cloning of $Ca^{2+}_o$-sensing receptor from chicken parathyroid and determination of its nucleotide and deduced amino acid sequences: Northern analysis was carried out on poly ($A^+$) RNA, isolated from parathyroid glands of vitamin D-deficient chickens, using the bovine CaR cDNA probe described in Materials and Methods. A single band of 6.2 kb was observed (FIG. 1a) indicating expression of calcium-sensing receptor mRNA in chicken as in mammalian parathyroid (Brown et al. Nature 336:575–580 (1993)). A size-selected, directional chicken parathyroid cDNA phage library obtained using the same RNA was constructed and screened and three independent positive clones with inserts larger than 5 kb, called C1D, C3A and C8A, were isolated. Restriction mapping showed that these three clones were closely related, differing only in the length of their 5' ends. The shortest of the three clones, C1D, was fully sequenced (FIGS. 2A–2D). This clone, 5046 nucleotides in length, has a single open reading frame (ORF) of 3177 nucleotides that begins with the initiation codon (AUG) within the Kozak sequence (GGAACAAUG) (Kozak, Nucl. Ac. Res. 12:857–872 (1984)) at nucleotide 87 and terminates at nucleotide 3263 (UAA terminator codon). C1D has an 18 nucleotide poly A tail and a polyadenylation signal (AAUAAA) located 23 nucleotides upstream of the poly A tail. The nucleotide coding region shares 79% sequence identity with the human CaR sequence.

The predicted protein coded by the ORF of the chicken CaR comprises 1059 amino acids. FIG. 3 provides a schematic representation of its principal features. The hydropathy profile and general topology of the receptor are similar to its mammalian homologs (Brown et al. Nature 336:575–580 (1993); Garrett, et al. Endocrinology 136:5202–5211 (1995); Riccardi, et al., Proc. Nat'l Acad. Sci. USA 92:131–135 (1995); Ruat et al., Proc. Nat'l Acad. Sci. USA 92:3161–3165 (1995)). The receptor contains three main domains: (a) a large, predominantly hydrophilic, amino-terminal domain comprising the first 611 amino acids; (b) a hydrophobic core of 249 amino acids that predicts seven helical transmembrane domains; and (c) a carboxyl-terminal hydrophilic domain comprising the last 198 amino acids which is slightly shorter than the other CaRs cloned to date. The amino-terminal domain is predicted to be extracellular since it includes a leader sequence of 19 hydrophobic amino acids characteristic of eukaryotic signal sequences. The extracellular domain also contains a 19 residue segment of hydrophobic amino acids (amino acids 136–165) characteristic of both calcium-sensing receptors and metabotropic glutamate receptors (mGluRs) (Brown et al. Nature 336:575–580 (1993); Nakanishi et al., Science 258:597–603 (1992)). This predicted protein structure exhibits the characteristics of the superfamily of G-protein coupled receptors (GPCRs).

The putative extracellular domains contain several clusters of acidic residues that may potentially be involved in cation binding (Fliegel, et al., Proc. Nat'l Acad. Sci. USA 84:1167–1171 (1987))—amino acids 79–80 EE, 126–127 DE, 190–191 DE, 215–217 DDD, 228–232 EEAEE, 249–251 EEE, 353–354 EE, 378–379 EE, 378–379 EE, 397–398 DE, 478–479 DE, 498–499 ED, 505–506 EE, 574–575 DE, 586–587 ED, and 756–758 EDE. The amino acid sequence predicts 12 potential extracellular N-glycosylation sites, one of which is present within the first extracellular loop. Five potential protein kinase C phosphorylation sites are found within the intracellular domains, including three within the carboxyl-terminal domain (Ser-793, Ser-894, Ser-914) and one each in the first (Thr-645) and third (Thr-698) intracellular loops. In addition, two potential cAMP-dependent protein kinase A phosphorylation sites were found at the carboxyl-terminal domain (Ser-898 and Ser-971).

The predicted protein sequence shows 84% overall identity to the human CaR (FIGS. 4A–4B). Two separate protein domains show significant differences in their amino acid sequences from other mammalian CaRs that have been cloned. A sequence in the mid region of the extracellular domain, comprising amino acids 359 to 390, shows little similarity to the human and other mammalian sequences. In addition, much of the sequence in the predicted, cytoplasmic carboxyl-terminal tail varies in both its length and amino acid sequence from mammalian homologs. A region of the human CaR enriched in glutamine residues (amino acids 925–961) is absent in the chicken CaR sequence and that last 60 amino acids of both sequences share little homology.

Figure 5:
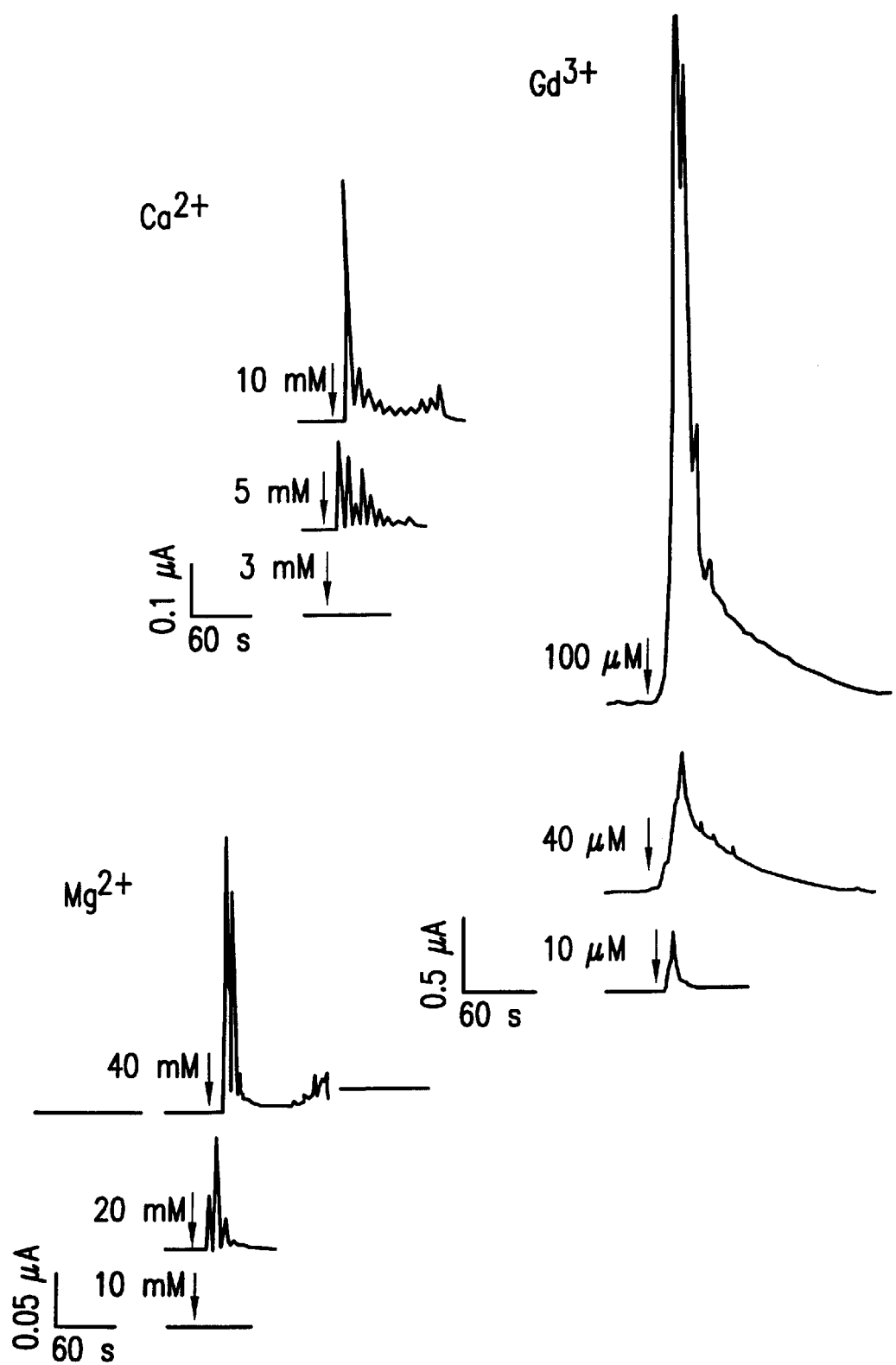
FIG. 5: Functional expression of the chicken CaR in Xenopus oocytes: $Gd^{3+}_o$, $Ca^{2+}_o$ and $Mg^{2+}_o$ elicit dose-dependent inward currents in oocytes injected with chicken CaR. The $Gd^{3+}_o$-mediated responses were almost an order of magnitude greater than the $Ca^{2+}_o$-evoked responses, which, in turn, were greater than the $Mg^{2+}_o$-mediated responses. Experiments were performed at least in duplicate using different oocytes.

Expression analysis: Despite its differences from the mammalian receptors in protein sequence, the chicken CaR is functionally active. *Xenopus laevis* oocytes that had been injected with synthetic chicken CaR RNA responded to exogenous polyvalent cations by producing transmembrane Cl⁻ currents. Examples of the responses of CaR cRNA-injected oocytes to increasing concentrations of $Ca^{2+}_o$, $Mg^{2+}_o$ or $Gd^{3+}_o$ are shown in FIG. 5. The oocytes' responses increased as the concentration of the added cation increased. Similar to the behavior of oocytes injected with cRNA for the bovine CaR (Brown, et al. *Nature* 366:575–580 (1993)), oocytes injected with the chicken CaR cRNA showed greatest sensitivity to $Gd^{3+}_o$ (half-maximal activation in the micromolar range). The responses to $Ca^{2+}_o$ and $Mg^{2+}_o$ were considerably lower in magnitude, both cations being effective in the millimolar range. No responses were elicited in the $H_2O$-injected oocytes.

Tissue distribution of CaR mRNA: In situ hybridization demonstrated the presence of chicken CaR message within parathyroid glands of the vitamin D-deficient chickens. A strong signal was obtained using an antisense riboprobe coding for the 5'-end of the coding sequence (FIG. 1*b*), whereas the corresponding sense probe showed no staining (FIG. 1*c*). There was a concentration of signal in cellular clusters, apparently indicating that large areas within the glands do not express transcripts for the receptor.

Figure 6:
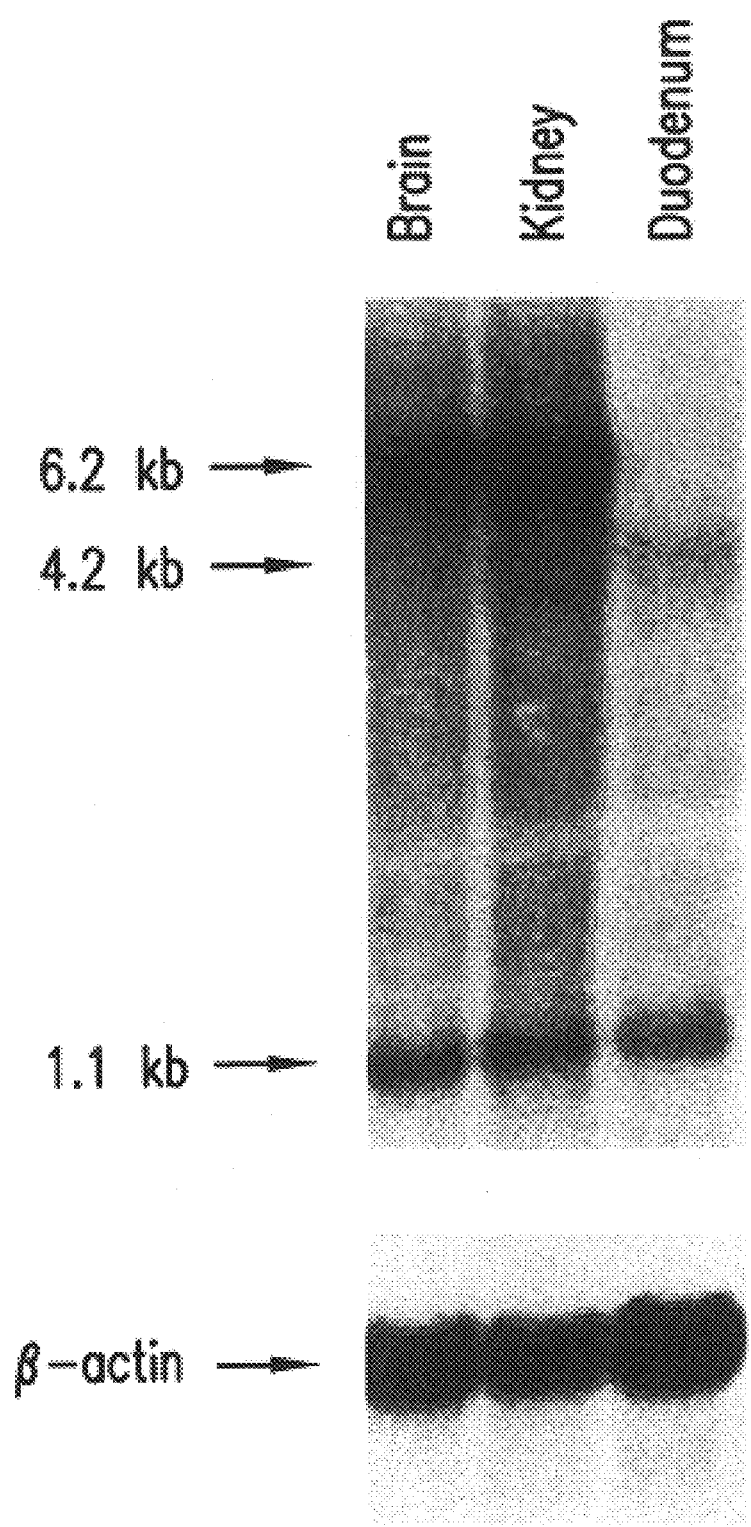
FIG. 6: Northern analysis of the chicken CaR in selected chicken tissues: Northern hybridization of poly(A+) RNA from chicken tissues (5 µg per lane) was carried out using a $^{32}$P-labeled riboprobe from the 5' portion of the coding region of the chicken CaR. The lower panel shows hybridization of the same blot with a β-actin probe.
Figure 7:
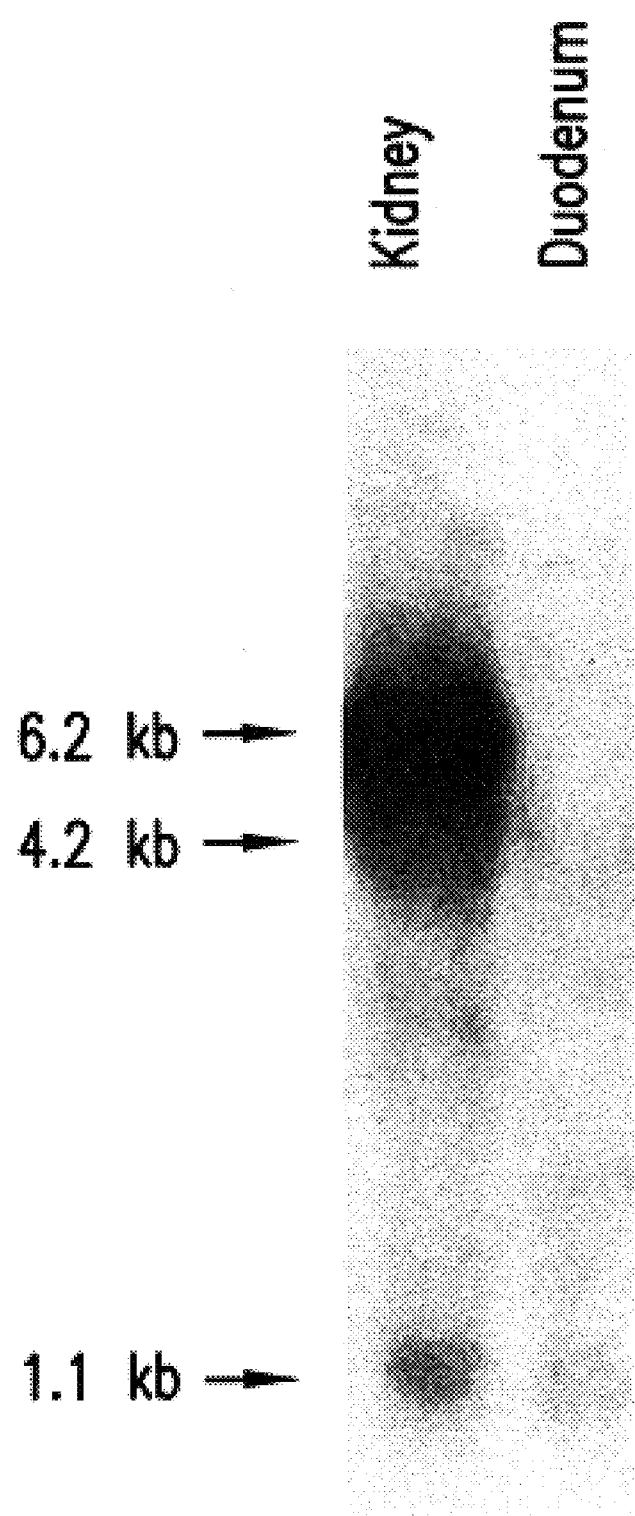
FIG. 7: Northern analysis of the chicken CaR in kidney and duodenum from a day-old chicken: Northern hybridization on poly(A+) RNA (5 µg per lane) was done with a $^{32}$P-labeled riboprobe from the 5' end region of chicken CaR as in FIG. 6.

Northern analysis of brain and kidney RNA of a laying chicken showed a major band of 6.2 kb similar to that present in parathyroid RNA and an additional band at 1.1 kb (FIG. 6). The 1.1 kb band was not observed when the sample was hybridized with a full length cDNA fragment instead of the riboprobe. In the duodenum, the riboprobe detected a 4.2 kb band. Northern analysis of the kidney and duodenum of a day-old chick (FIG. 7) showed a 6.2 kb and a 4.2 kb band, respectively, and a 1.1 band, similar to the samples taken from tissues of the laying hen (FIG. 6).

Figure 8A:
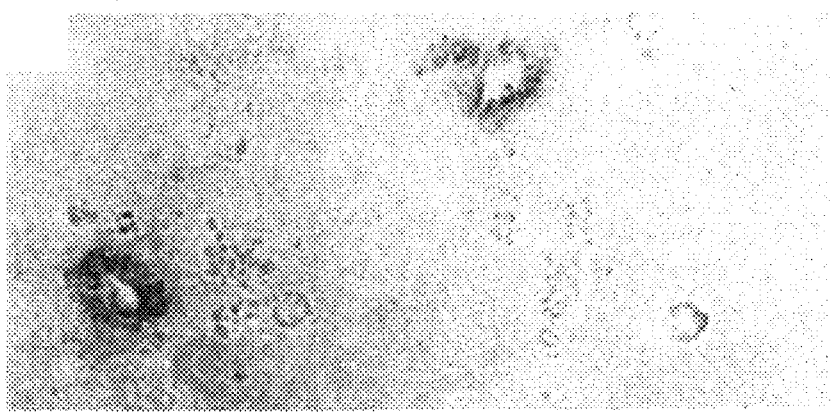
FIGS. 8(a)–8(c): Immunohistochemical demonstration of the CaR in chicken kidney using an anti-CaR antibody: Immunohistochemistry on 4 µm frozen sections from adult chicken kidney was performed using a monoclonal antibody against CaR. (8a) Cross-sectional view of kidney parenchyma stained with anti-CaR monoclonal antibody showing strong staining of the epithelial lining of some tubules. (8b) A similar view is shown of the kidney parenchyma when the monoclonal antibody was preabsorbed with specific peptide. (8c) Hematoxylin staining of an equivalent section from kidney showing the general morphological organization of tubular and glomerular structures (400×).
Figure 8B:
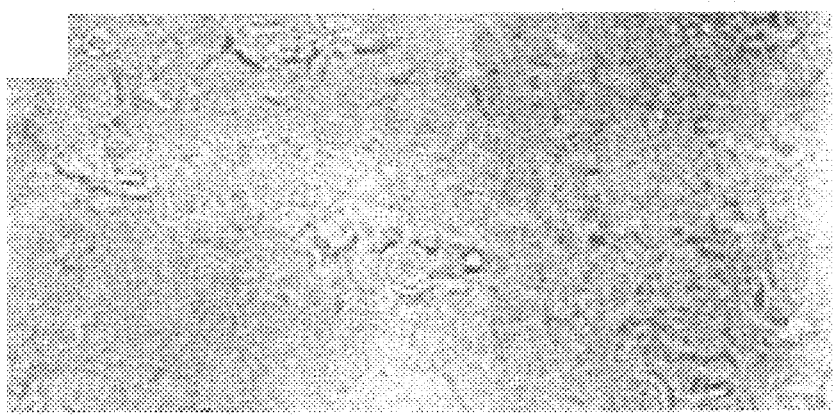
Figure 8C:
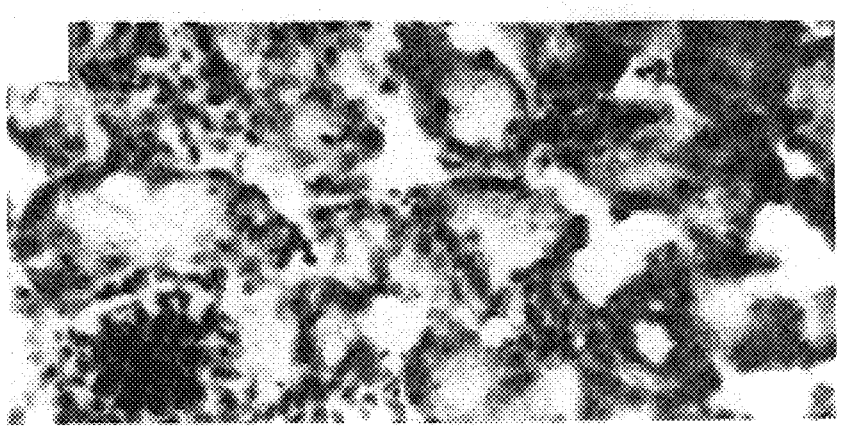

Immunohistochemistry of CaR in Kidney: In view of the non-uniformity of CaR distribution along the renal tubule of the mammalian kidney, receptor expression was evaluated by immunohistochemistry. A section through the kidney of a laying hen is shown in FIGS. 8*a*–8*c*. Some tubular cellular structures were immunostained by a monoclonal antibody that recognizes the CaR (FIG. 8*a*). Preabsorption of the antibody with its specific antigen abolished specific staining, indicating specificity of the procedure (FIG. 8*b*). Glomerular structures and a large proportion of the tubular structures examined did not stain with the antibody.

Discussion

The level at which the extracellular ionic calcium concentration is maintained is highly conserved in both mammalian and non-mammalian species. Total plasma calcium in growing chickens is 10 mg/dl similar to that in mammals. However, plasma $Ca^{2+}$ exceeds 20 mg/dl in the female bird during reproduction due to the appearance in the plasma of the yolk protein precursor, vitellogenin-A, a $Ca^{2+}$ binding protein. Despite these changes in total plasma $Ca^{2+}$, ionized calcium remains unchanged—between 1.2 and 1.3 mmol.

The predicted amino acid sequence of the chicken CaR is similar to that of the human receptor (FIGS. 4A–4B). The two receptors share 79 and 84% identical nucleotide and amino acid sequences, respectively. However, a degree of sequence homology of over 90% is usually found among mammalian species (Aida, et al., *J. Endocrinol. Metab.* 80:2594–2598 (1995); Brown et al.*Nature* 336:575–580 (1993); Garrett, et al. *Endocrinology* 136:5202–5211 (1995); Riccardi, et al., *Proc. Nat'l Acad. Sci. USA* 92:131–135 (1995); Ruat et al., *Proc. Nat'l Acad. Sci. USA* 92:3161–3165 (1995)).

The predicted topology for the chicken CaR closely resembles its mammalian counterparts. The protein contains a large extracellular amino-terminal domain, seven transmembrane domains and a cytoplasmic carboxyl-terminal domain, typical of the superfamily of GPCRs. Of the highly conserved regions in the molecule, the one between amino acids 91 and 250, located in the extracellular region, includes a large hydrophobic region that is also present in mG1uR (Brown et al. *Nature* 336:575–580 (1993); Nakanishi et al., *Science* 258:597–603 (1992)). The majority of the non-conserved regions of sequence, when comparing the mammalian and chicken CaRs, are concentrated within the intracellular carboxyl-terminal tail, which is involved in G-protein coupling, and the amino-terminal signal peptide. The chicken CaR contains another stretch of 30 amino acids in the mid region of the extracellular domain (amino acids 360–390) that has little homology to those of its mammalian homologs. The first half of the extracellular domain is the region of the human receptor within which several point mutations in the hypercalcemic disorder, FHH, produce rightward shifts in the level of $Ca^{2+}_o$ necessary to elicit a given increase in intracellular $Ca^{2+}$ in response to exogenous polycations (Aida, et al., *J. Endocrinol. Metab.* 80:2594–2598 (1995); Pollak, et al., *J. Clin. Invest.* 93:1108–1112 (1994)). This region of the sequence and these residues, in particular, are fully conserved between the human and chicken CaRs.

Cation binding to the CaR has been postulated to occur in the extracellular domain. The mammalian receptor contains several clusters of acidic amino acids similar to those thought to be involved in low affinity $Ca^{2+}$ binding by proteins such as calsequestrin (Fliegel, et al., *Proc. Nat'l Acad. Sci. USA* 84:1167–1171 (1987)). The chicken CaR contains similar clusters of acidic amino acid residues that are conserved among all currently characterized mammalian CaRs. The chicken contains various sites that are targets for post-translational modification. The extracellular domain bears 12 potential glycosylation sites. The intracellular loops and the cytoplasmic carboxyl-terminal domain are potential targets for phosphorylation by both protein kinase C and protein kinase A. Receptor phosphorylation is a well-described mechanism for down regulation of receptor activity in various receptor-coupled pathways. Activation of protein kinase C partially reverses the inhibition of parathyroid hormone secretion by extracellular calcium (Racke, et al., *Am. J. Physiol.* 267:E429–438 (1994)), and this may be one of the possible mechanisms for the down regulation of the function of the CaR. Among the characterized mammalian CaRs, all contain both protein kinase C and protein kinase A phosphorylation sites with the exception of the bovine CaR, which only has only four PKC and no PKA sites. The carboxyl-terminal domain of the chicken CaR is shorter than its mammalian counterpart. This domain may play a role in G-protein binding or activation; however, the significance of size and amino acid content have not been defined sufficiently well to predict potential G-protein binding specificity.

Expression of the chicken CaR cRNA in *X. laevis* oocytes confirmed the ability of the cloned chicken CaR to activate Cl⁻ currents in response to addition of polycationic agonists similar to the other CaRs tested to date (Brown, et al., *Nature* 366:575–580 (1993); Riccardi, et al. *Proc. Nat'l Acad. Sci. USA* 92:131–135 (1995)), presumably through G protein-dependent activation of phospholipase C. The receptor was most sensitive to extracellular $Gd^{3+}$, which activated the CaR in the micromolar range. Responses to both $Ca^{2+}_o$ and $Mg^{2+}_o$ were more moderate and occurred in the millimolar range. This pattern of responses was similar to those of the mammalian CaRs, apparently reflecting the fact that the levels at which the extracellular ionized calcium concentration is set are similar in mammals and chickens (Brown, et al., *Nature* 366:575–580 (1993); Riccardi, et al. *Proc. Nat'l Acad. Sci. USA* 92:131–135 (1995)).

The distribution of CaR expression in chicken is similar to that observed in mammalian species (Brown, et al., *Nature* 366:575–580 (1993); Riccardi, et al. *Proc. Nat'l Acad. Sci. USA* 92:131–135 (1995)). The receptor is expressed in organs associated with calcium homeostasis such as the parathyroid, kidney and intestine, although the non-uniform labeling of the chicken parathyroid gland by in situ hybridization raises the possibility that the expression of the receptor varies among chief cells. Interestingly, the size of the predominant transcript observed in the intestine was different from that present in the other tissues examined (4.2 Kb vs. 6.2 Kb). A similarly shorter band is also present in rat and rabbit intestine and rat kidney (Mithal, et al., *Endocrinology* 136:3087–3092 (1995)). The 4.2 kb transcript may represent an alternatively spliced product of the same gene or be the product of a related gene that shares a similar 5' domain. The 1.1 kb transcript appeared in all blots that were hybridized with the riboprobe.

In the parathyroid, the CaR has been implicated in the regulation of PTH secretion (Brown, et al., *Physiol. Rev.* 11:333–337 (1991); Brown, et al., *Nature* 366:575–580 (1993)). In the kidney, the receptor may be associated with the regulation of urinary calcium excretion, on the one hand, and with the synthesis of $1,25\ (OH)_2D_3$, on the other (Brown, et. al., *New Eng. J. Med.* 366:234–240 (1995)). In the intestine, the receptor may conceivably be associated with the non vitamin D-dependent regulation of $Ca^{2+}$ absorption that is observed during the egg cycle in the laying hen (Bar, et al., *J. Nutr.* 106:1332–1338 (1976; Hurwitz, et al., *Am. J. Physiol.* 225:140–154 (1973)).

The expression of the CaR is not restricted to tissues associated with mineral ion homeostasis; chicken brain, like rat brain, expressed readily detectable levels of messenger RNA for the CaR. The receptor in brain has been implicated in synaptic transmission (Brown, et al., *Cell* 83:679–682 (1995)) as well as in the regulation of the activity of a calcium permeable, nonselective cation channel (Ye, et al., *Biochem. Biophys. Res. Comm.* 224:271–280 (1996); Ye et al., *Biochem. Biophys. Res. Comm.* 226:572–579 (1996)).

Example 2

Regulation of Calcium Binding by Transfected With DNA Encoding Human CaR

Materials and Methods

Culturing and maintenance of HEK 293. HEK 293 cell lines were grown in DMEM with 10% fetal bovine serum and 200 nM hygromycin and were passaged weekly.

Measurement of $Ca_i$ using cell population system: Coverslips with near-confluent HEK cells were loaded with fura-2/AM and placed diagonally into thermostated cuvettes equipped with a magnetic stirrer. The bath solution was stirred at 37° C., and CaR agonists were added to the desired final concentration. Excitation monochromers was centered at 340 nm and 380 nm with emission light collected at 90° using a long-pass emission filter. The 340/380 excitation ratio of emitted light was used to calculate $Ca_i$. Both in vivo and in vitro calibrations were used to estimate $Ca_i$.

Measurement of $^3H$-inositol phosphates: Cells transfected with DNA encoding human CaR were labeled with [$^3H$] inositol (10 uCi/$10^6$ cells) overnight in medium 199 (with 10 ul/ml penicillin-streptomycin, 10 mM Hepes, pH 7.5, and 15% bovine serum), washed with solution (10 mM LiCl, 0.5 mM $MgSO_4$, 0.5 mM $CaCl_2$, and 2 mg/ml BSA in Eagle's MEM with Earle's salts), and then incubated with polyvalent cations for 30 minutes. Reactions were terminated with a final concentration of 10% TCA. After sedimentation of precipitated debris and removal of TCA by ether extraction, inositol phosphates in the aqueous phase were separated on Dowex anion exchange columns. The radioactive inositol monophosphate (InsP), bisphosphate ($InsP_2$), trisphosphate ($InsP_3$) and tetraphosphate ($InsP_4$) were eluted stepwise with 0.2 M, 0.4 M, 0.8 M and 1.2 M formate containing 0.1 M formic acid, respectively, and quantitated using a liquid scintillation counter.

Results

Figure 10A:
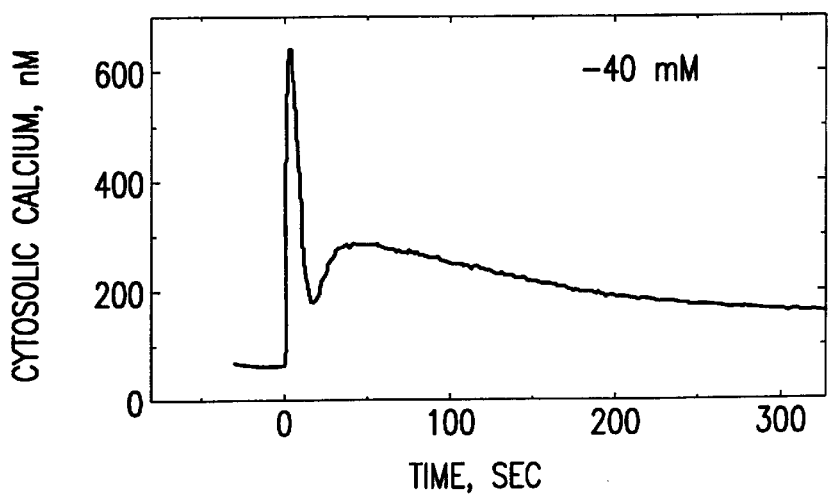
FIGS. 10a–10d: Effects of ionic strength on the cytosolic calcium response to external calcium stimulation of HEK 293 cells expressing the CaR: (10a–10c) A clonal HEK 293 cell line stably transfected with the human CaR was used to test the effects of ionic strength on activation of CaR. External calcium was elevated from 0.5 to 2.5 mM immediately prior to the $Ca_i$ transient and was maintained for the duration of the recording. The concentration of NaCl was adjusted by the addition of 20 to 60 mM NaCl or the removal of 20 to 60 mM NaCl. Osmolality was not held constant. (10b) The ionic strength-calcium response relationship was determined over a range of NaCl concentrations. Both peak and sustained cytosolic calcium changes showed an inverse relationship to ionic strength. The experiments were performed in media including 125 mM NaCl with an osmolality of 280–290 mOsm and a pH of 7.4.
Figure 10B:
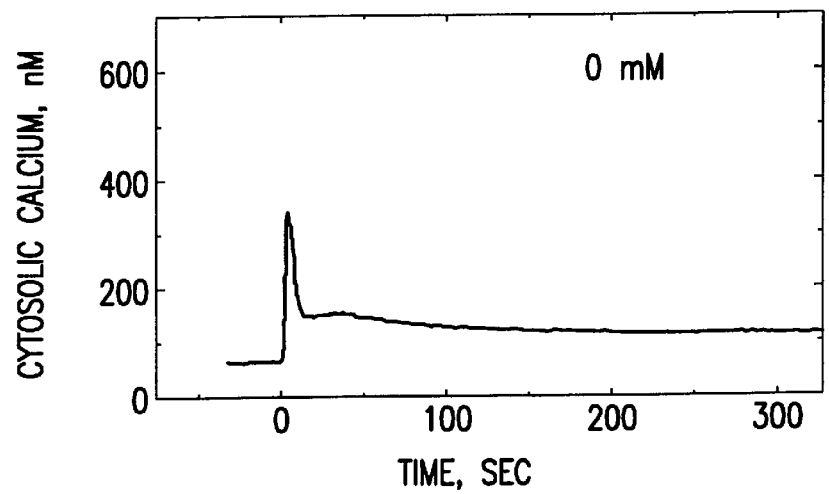
Figure 10C:
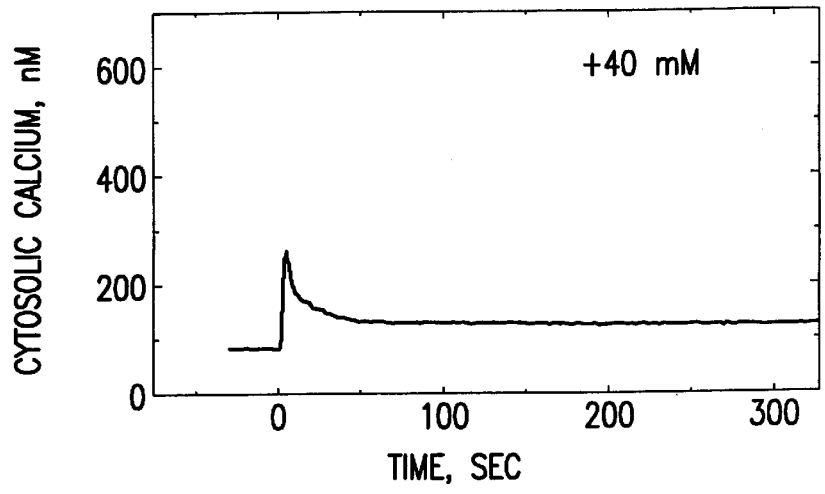
Figure 10D:
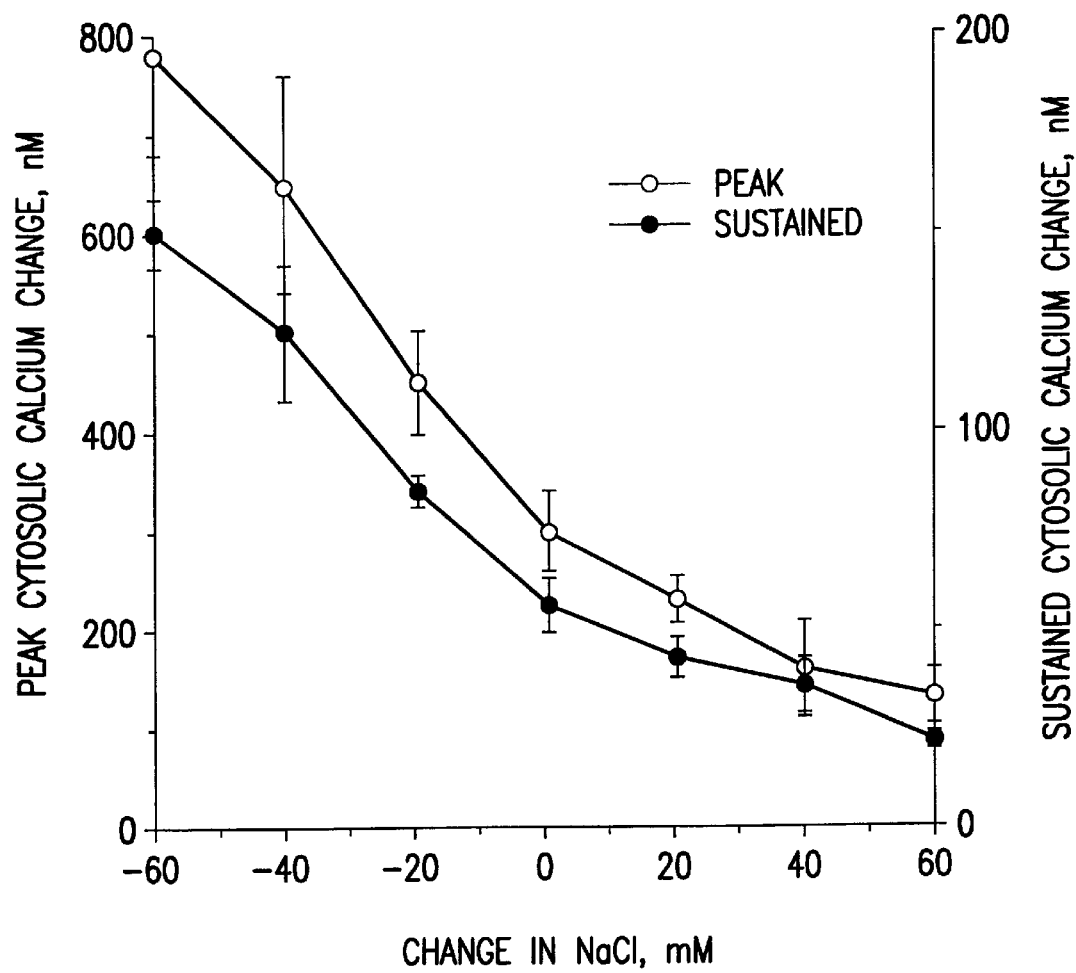

Effect of NaCl on agonist-evoked activation of the calcium-sensing receptor: The effect of ionic strength on activation of the calcium-sensing receptor by external $Ca^{2+}$ ($Ca_o$) was studied by adding or removing NaCl from the extracellular media followed by the elevation of $Ca_o$. Changes in cytosolic calcium ($Ca_i$) were used as an indicator of CaR activation in CaR-expressing HEK cells. Osmolality was not held constant in these experiments. Instead, ionic strength and osmolality were allowed to change concomitantly, as would occur in vivo. FIGS. 10a–10c shows the effect of changing the concentration of NaCl on activation of the CaR by 2.5 mM $Ca_o$ in HEK 293 cells stably transfected with the human CaR. When NaCl is elevated, the $Ca_i$ response to 2.5 mM $Ca_o$ is attenuated, whereas removal of NaCl produces an enhanced response. The dose-dependency of external NaCl effects on CaR activation by $Ca_o$ is shown in FIG. 10d. The results indicate that peak $Ca_i$ increases are modulated in a similar direction and magnitude by changes in NaCl concentration.

Figure 11A:
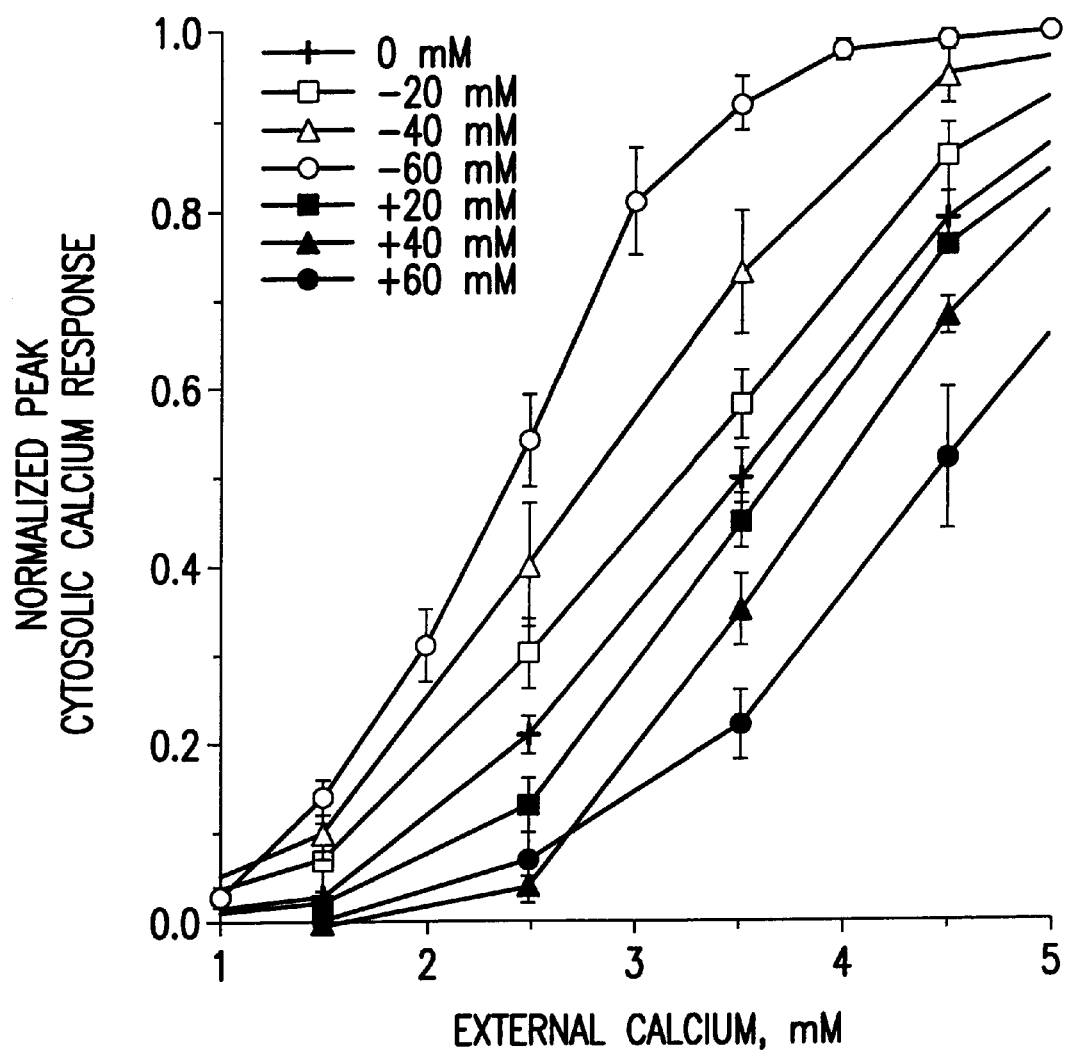
FIGS. 11a–11b: Effect of ionic strength on the external calcium sensitivity of HEK cells expressing CaR: (11a) Concentration-response curves were determined for $Ca_0$ stimulation in the presence of different concentrations of NaCl, resulting in changes in ionic strength. With addition of NaCl and increased ionic strength, the CaR becomes less sensitive to $Ca_0$. The reverse was true for the reduction of NaCl and the lowering of ionic strength. $EC_{50}$ values ranged from 2.5 to 4.5 mM $Ca_0$ for the NaCl concentrations tested in these experiments. The experiments were performed in media including 65 to 185 mM NaCl and a pH of 7.4. Osmolality was not corrected in these experiments. (11b) The plot of $EC_{50}$ versus NaCl concentration shows an inverse relationship which is independent of osmolality. For hypoosmotic and hyperosmotic solutions, NaCl changes were not accompanied by any other modification of the media. For isoosomotic solutions, removal of NaCl included substitution by sucrose in a 2:1 ratio to maintain osmolality. For isosmotic addition of NaCl, the base solution included 200 mM sucrose and sucrose was replaced by NaCl in a 2:1 ratio.
Figure 11B:
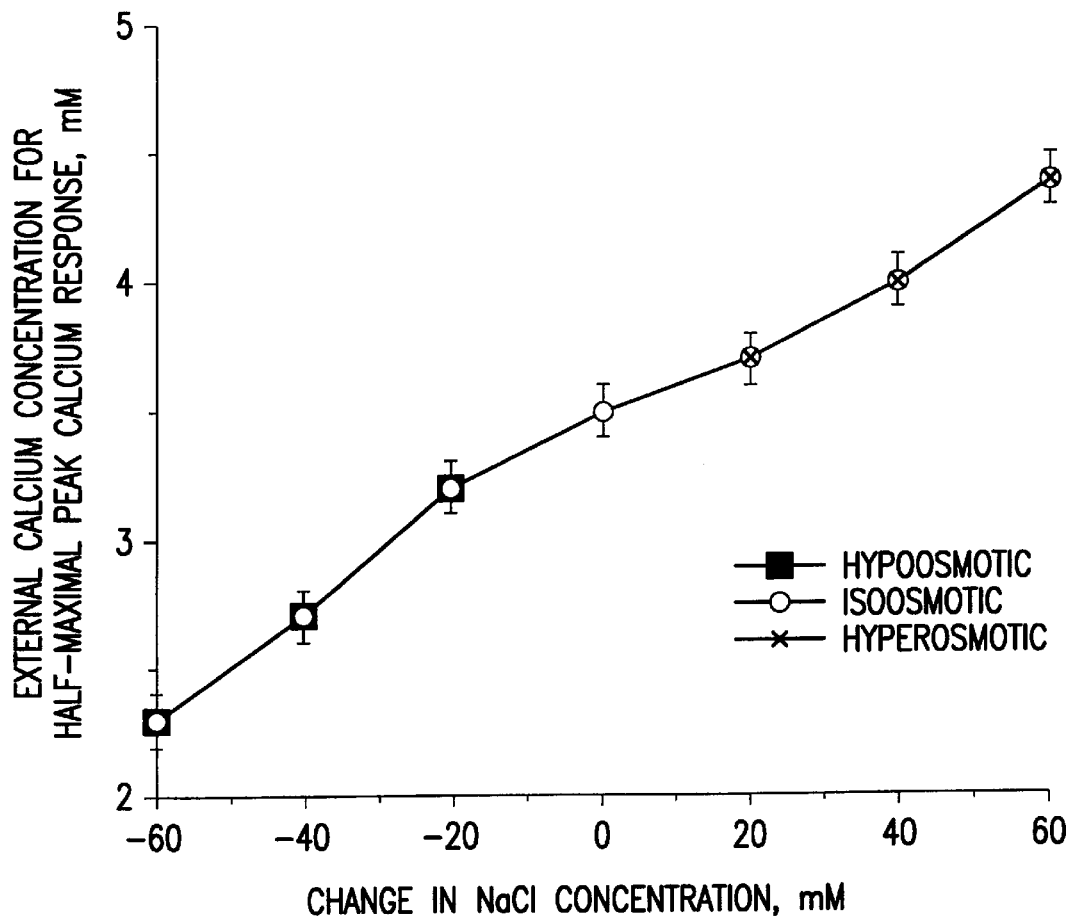

The concentration-response relationship for activation of the CaR by $Ca_o$ was compared in the presence of varying concentrations of NaCl (FIG. 11a). With no alteration in NaCl, the threshold for cell activation is about 1.5 mM calcium with an $EC_{50}$ of about 3.5 mM calcium. With addition of NaCl in 20 mM increments, the threshold and $EC_{50}$ both shift to the right, suggesting either a change in the CaR or the ability of $Ca_o$ to activate the receptor. The change in $EC_{50}$ was linear with changes in NaCl (FIG. 11b). Experiments were also performed maintaining osmolality constant while NaCl was varied in the extracellular media. For removal of NaCl, the NaCl was substituted by sucrose (i.e., 20 mM NaCl was replaced by 40 mM sucrose). Similarly, addition of NaCl involved replacement of sucrose from a Hepes-buffered solution containing an additional 200 mM sucrose (i.e., 40 mM sucrose was replaced by 20 mM NaCl). The CaR-expressing HEK cells responded in a similar manner to $Ca_o$ in solutions with or without the additional 200 mM sucrose. FIG. 11b shows that osmolality per se had no effect on CaR activation, since hyperosmotic and hypoosmotic changes in NaCl produced the same shifts in the dose-response relationship as did the same changes in NaCl under isosmotic conditions. Untransfected HEK 293 cells exhibited no change in $Ca_i$ in any of the test solutions regardless of changes in osmolality or NaCl.

Figure 12A:
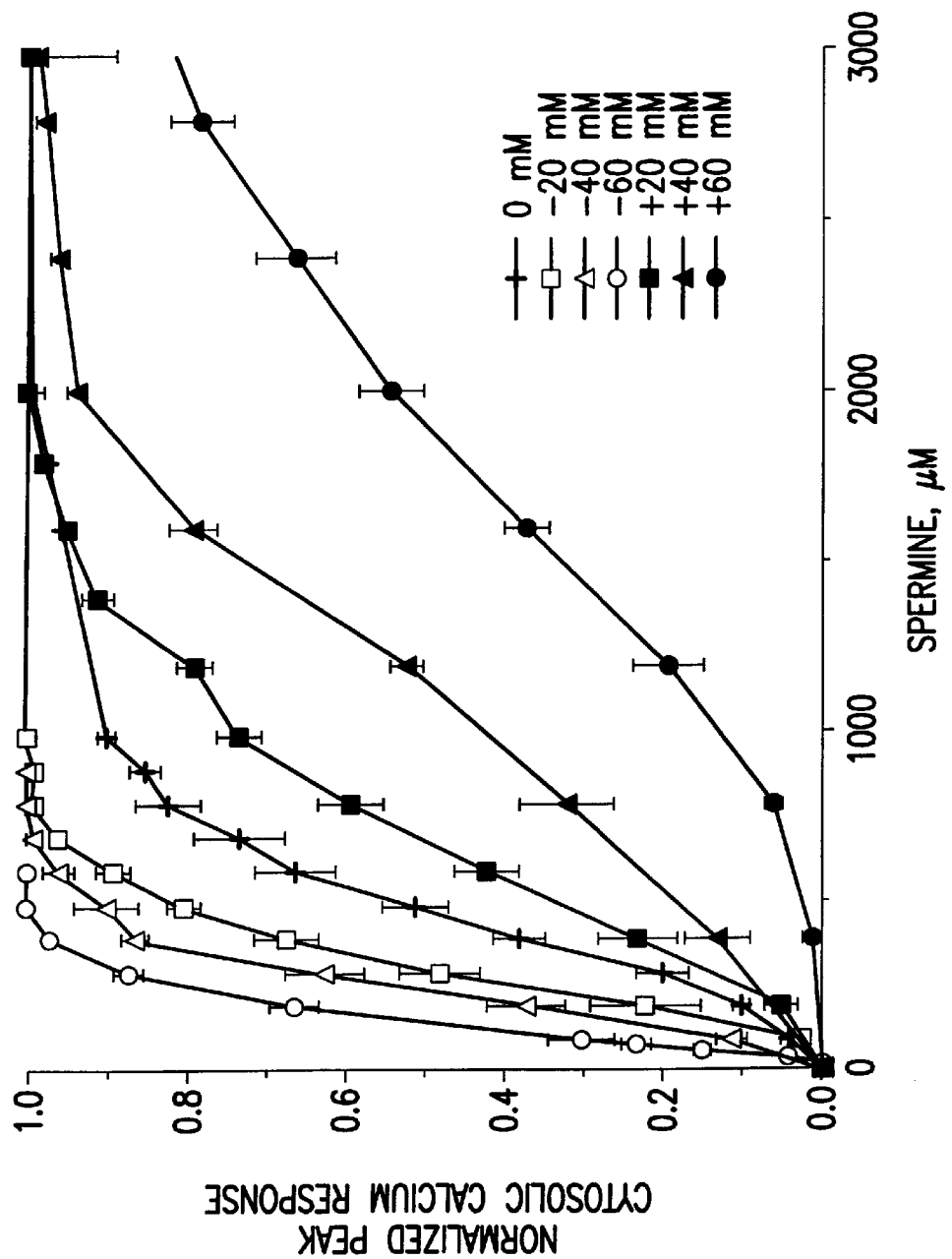
FIGS. 12a–12b: Effect of ionic strength on the spermine sensitivity of HEK cells expressing CaR: (12a) Concentration-response curves were determined for spermine stimulation in the presence of different concentrations of NaCl. With addition of NaCl and increased ionic strength, the CaR becomes less sensitive to spermine, while the reverse was true for the reduction of NaCl and the lowering of ionic strength. $EC_{50}$ values range from 200 to 2000 µM spermine for the NaCl concentrations tested in these experiments. (12b) The plot of $EC_{50}$ versus NaCl concentration shows an inverse relationship. The experiments were performed in media including 65 to 185 mM NaCl and a pH of 7.4. Osmolality was not corrected in these experiments.
Figure 12B:
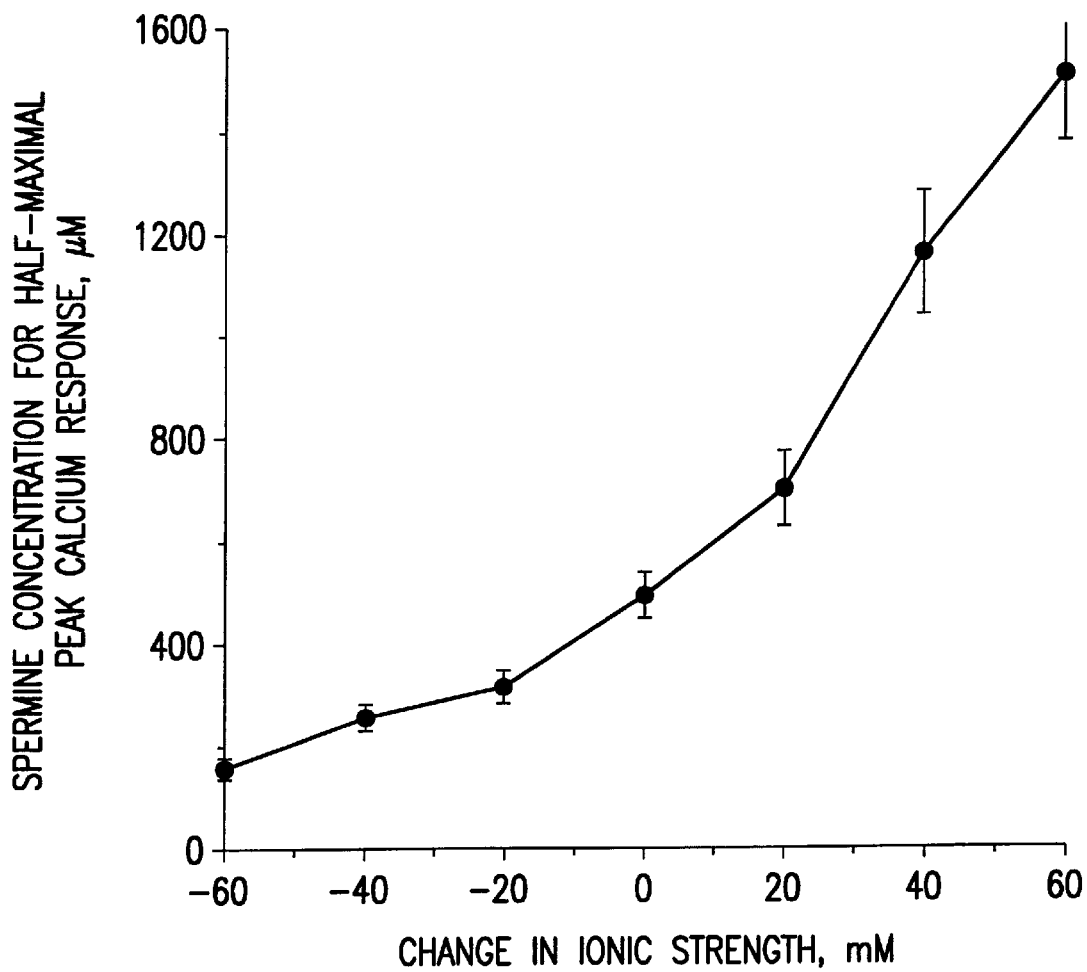

Agonist activation of the CaR leads to stimulation of phospholipase C and increased production of inositol phosphates in CaR-transfected HEK cells as well as cells expressing the receptor endogenously. To ensure that the ionic strength effect is specific to the activation of the CaR, inositol phosphate production was also examined during stimulation in the presence of different NaCl concentrations. As with the $Ca_o$ responses, inositol phosphate accumulation was also shifted in a similar manner, with enhanced accumulation observed with decreased ionic strength and the converse with increased ionic strength (FIGS. 12a–12b).

Figure 13A:
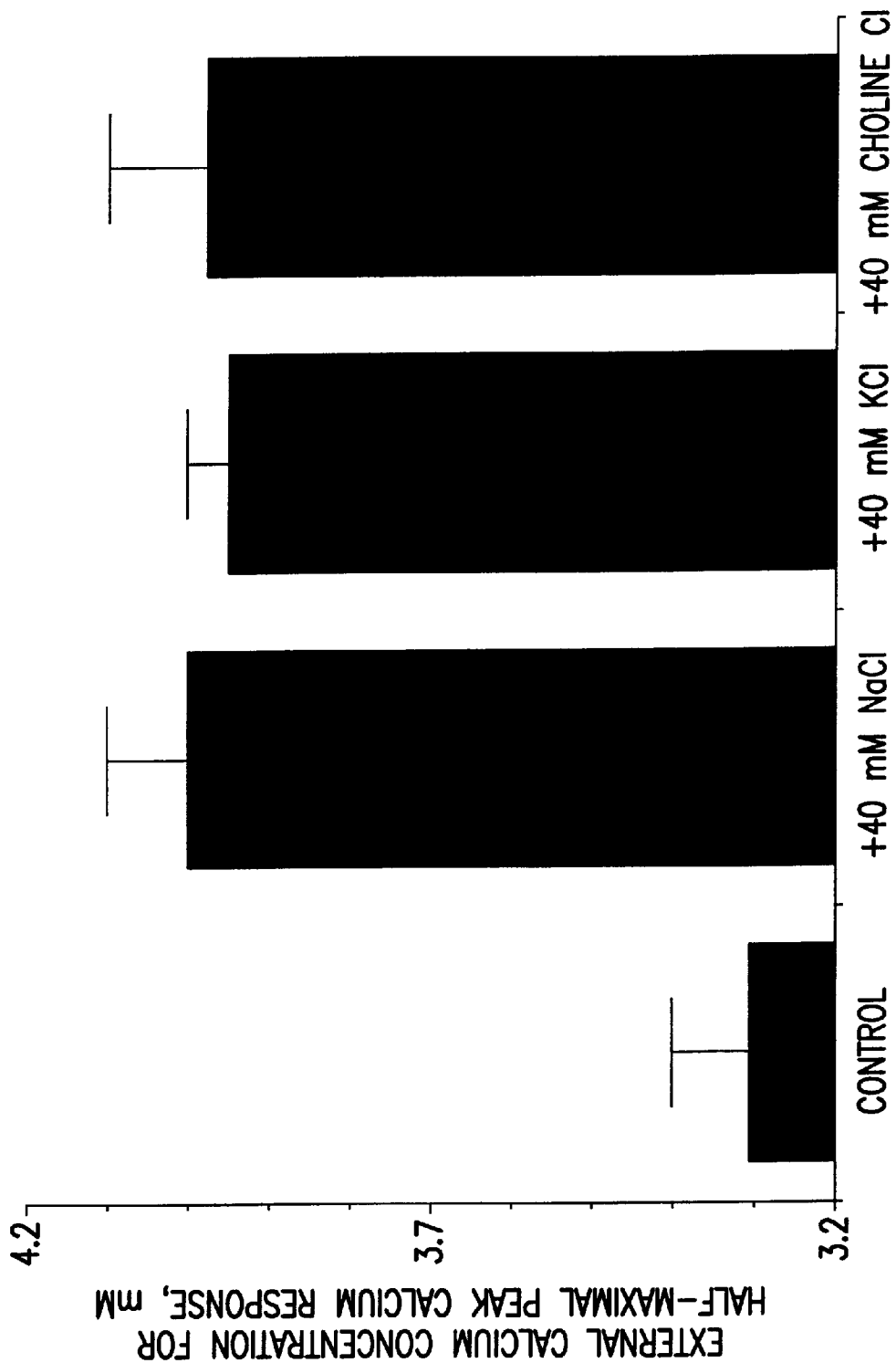
FIGS. 13a–13b: Effect of different cations and anions on the external calcium activation of HEK cells expressing human CaR: (13a) Addition of salts containing different cations produced similar shifts in the concentration-response relationship for $Ca_0$ activation of CaR. (13b) Addition of salts containing different anions produced similar shifts in the concentration-response relationship for $Ca_0$ activation of CaR. Control experiments were performed in media including 1 to 5 mM NaCl with an osmolality of 280–290 mOsm and a pH of 7.4. The different salts were added hyperosmotically to the control media.
Figure 13B:
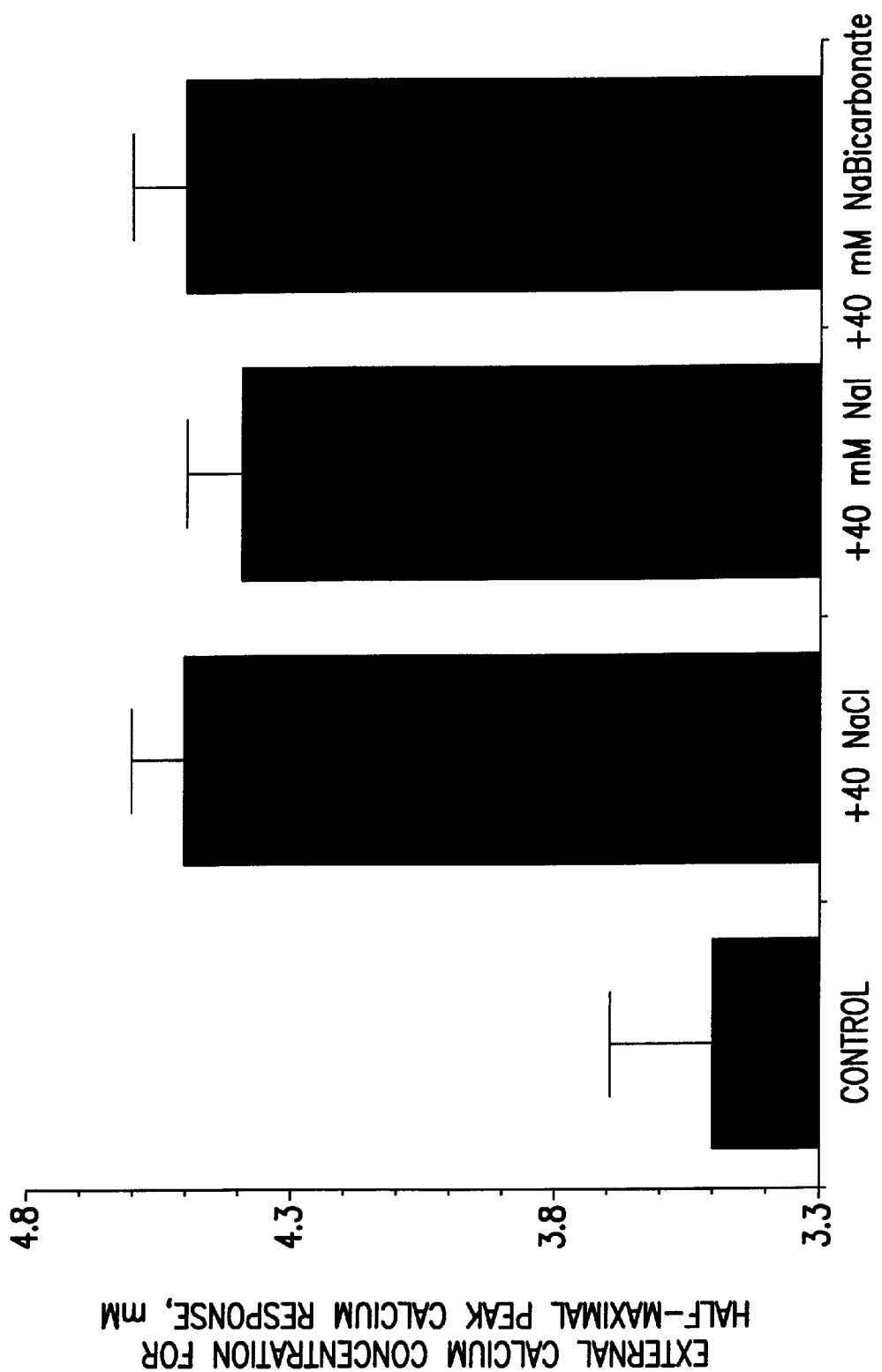

Sensing of ionic strength: The effects of NaCl may involve a sensor of sodium, chloride or ionic strength. Different salts were used to determine the mechanism of the NaCl effect. Addition of 40 mM choline chloride or potassium chloride had the same effect on the $EC_{50}$ of activation of the CaR-transfected HEK cells by $Ca_o$ as did addition of 40 mM NaCl (FIG. 13a). Likewise the addition of 40 mM sodium iodide or 40 mM sodium bicarbonate had similar effects as did 40 mM NaCl (FIG. 13b). These data indicate that neither sodium nor chloride are specific modulators of CaR activation. Instead, it is the change in ionic strength which modifies the activation of the CaR by $Ca_o$.

Figure 14:
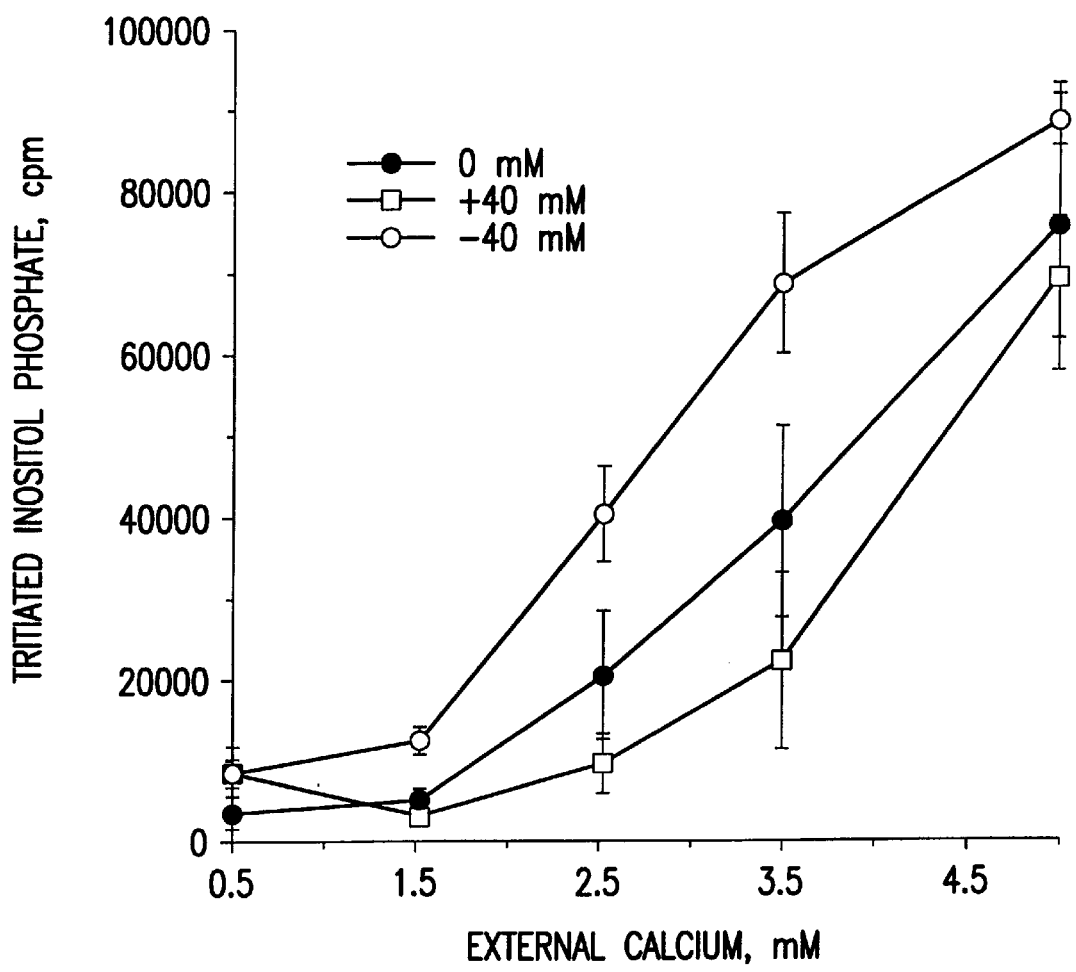
FIG. 14: Ionic strength modulation of external calcium stimulation of inositol phosphate (IP) accumulation in HEK 293 cells expressing CaR: Increased production of inositol phosphates were observed during stimulation of CaR-transfected HEK cells with $Ca_0$. This $Ca_0$ effect was potentiated by decreasing the NaCl concentration and attenuated by addition of NaCl.

Ionic strength modulation of CaR activation by spermine: Two broad classes of CaR agonists are polyvalent cations (i.e. $Ca^{2+}$ and $Gd^{3+}$) and polycationic molecules (i.e. spermine and neomycin). To test the generality of effects of ionic strength on CaR activation, the CaR-transfected HEK cells were stimulated by spermine in the presence of varying concentrations of NaCl. Similar to the effects on $Ca_o$ activation, ionic strength shifted the dose-response relationship for spermine so that the $EC_{50}$ was inversely proportional to the ionic strength (FIG. 14). In the case of spermine, the relationship between ionic strength and $EC_{50}$ was clearly nonlinear, a trend that may be magnified by the multiple positive charges spaced out along the spermine molecule.

Figure 15:
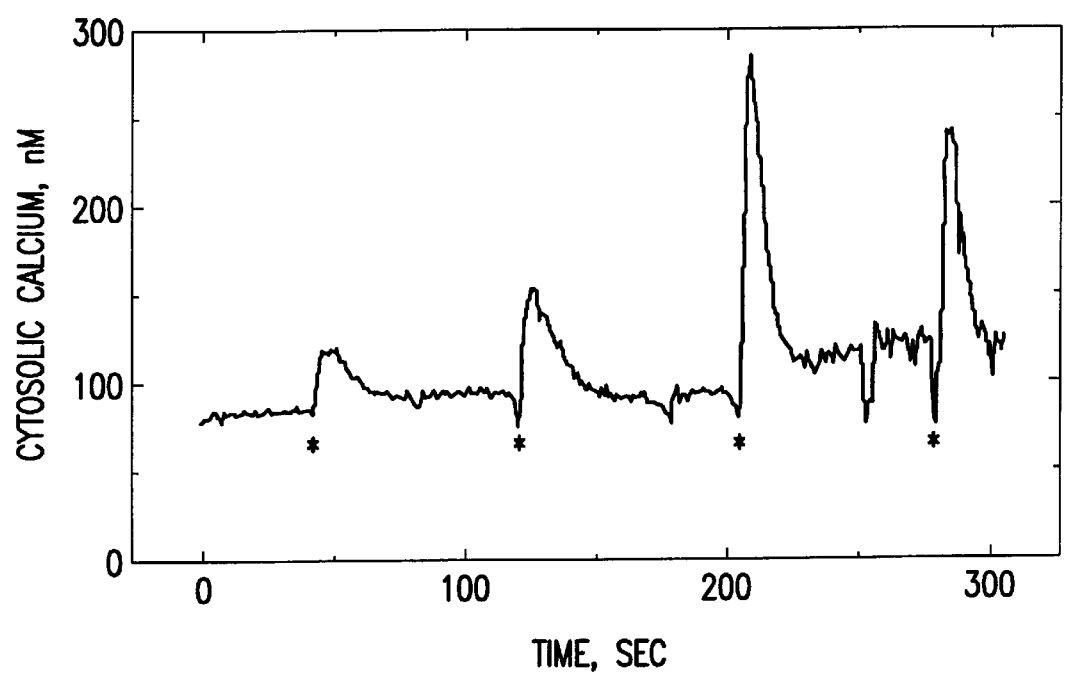
FIG. 15: Activation of CaR expressed in HEK cells by the lowering of ionic strength: The cytosolic calcium recording shows transients elicited by incremental 20 mM decreases in NaCl in the absence of external calcium and magnesium. The experiments were performed in media including 45 to 125 mM NaCl and a pH of 7.4. Osmolality was not corrected in these experiments.

Ionic strength and the activity of the calcium-sensing receptor: Ionic strength may affect both the soluble ligand by screening its positive charges as well as the CaR itself by screening charged residues. To study the effects of ionic strength alone, experiments were performed with no addition of divalent cations to the extracellular solution to act as a polyvalent ligand for the CaR (FIG. 15). Decreasing ionic strength produced a $Ca_i$ response similar to that found with agonist stimulation of the CaR which was dependent on the magnitude of the change in ionic strength.

Figure 16A:
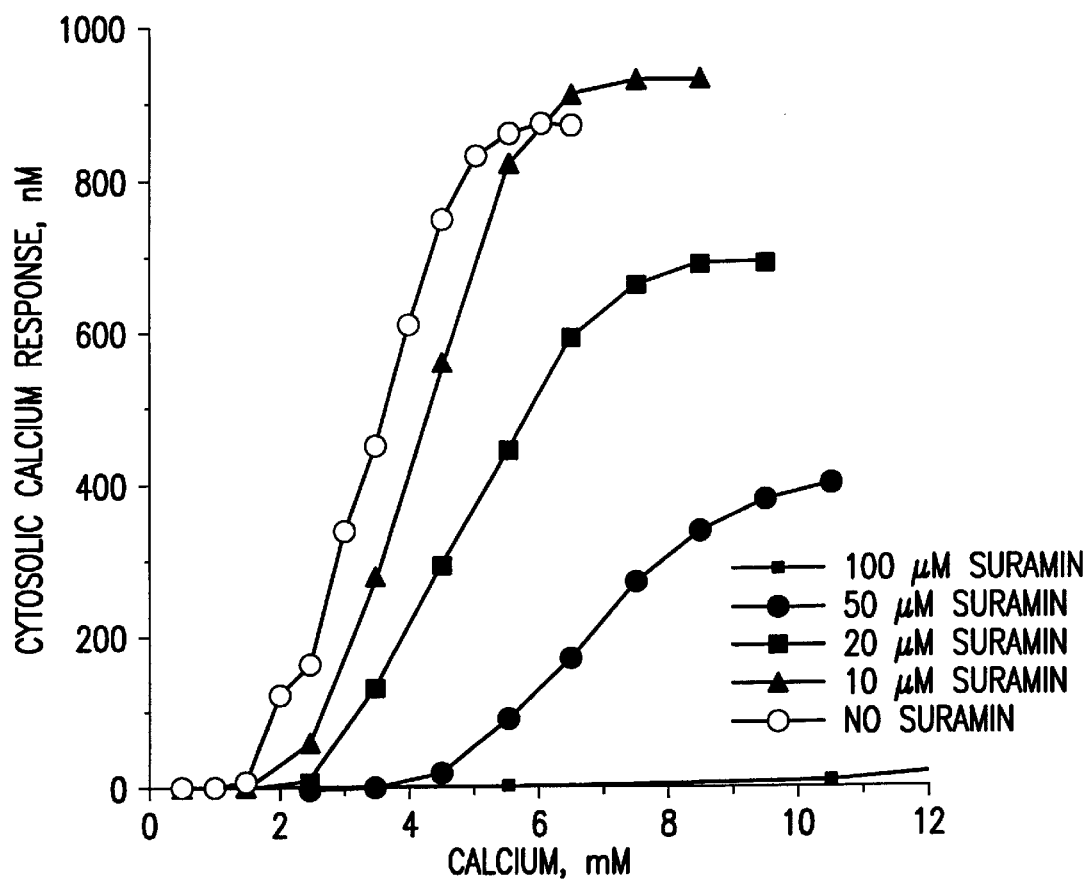
FIGS. 16a–16b: Effect of suramin on CaR responsiveness to extracellular calcium: The effect of increasing concentrations of suramin on the cytosolic calcium response of CaR-transfected HEK cells to changes in extracellular calcium concentration was studied and results are shown in Suramin, at concentrations of 17 to 100 µM, progressively decreases both the peak cytosolic response as well as the $EC_{50}$ of CaR to external calcium.
Figure 16B:
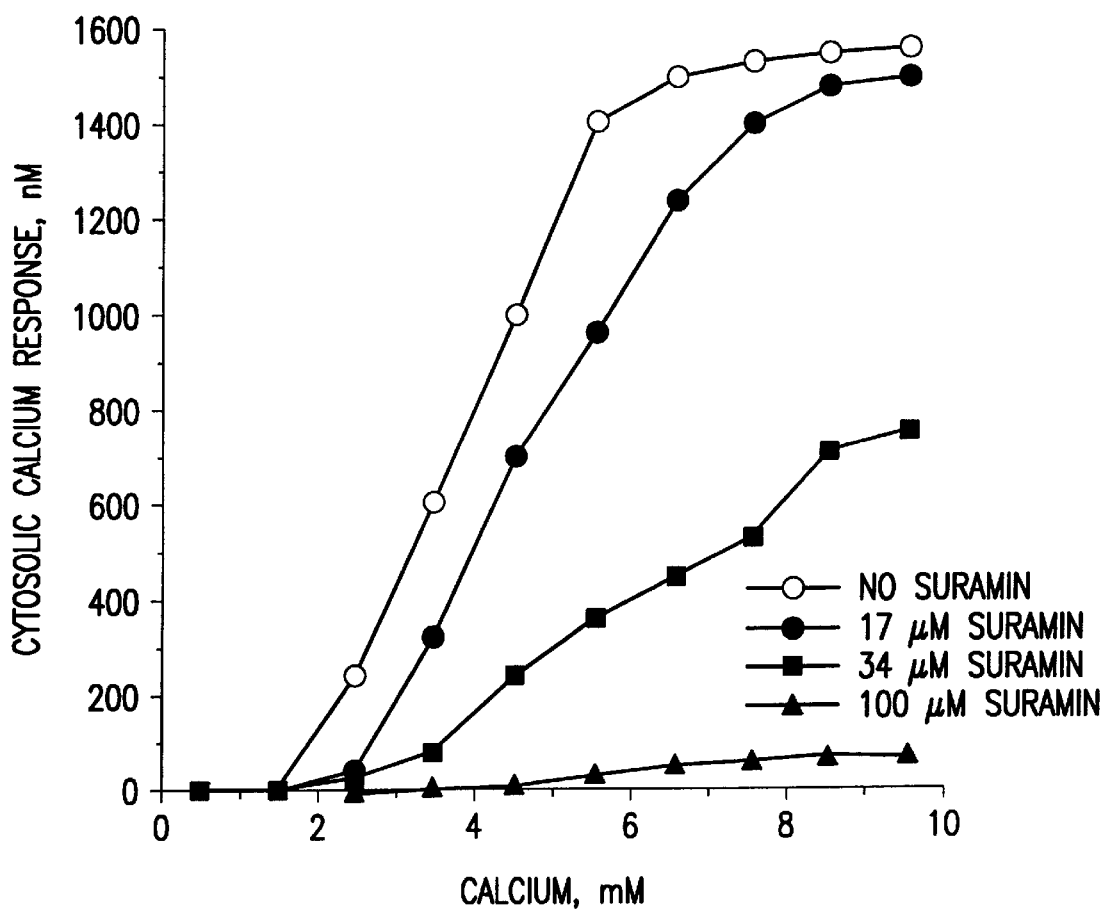
Figure 17:
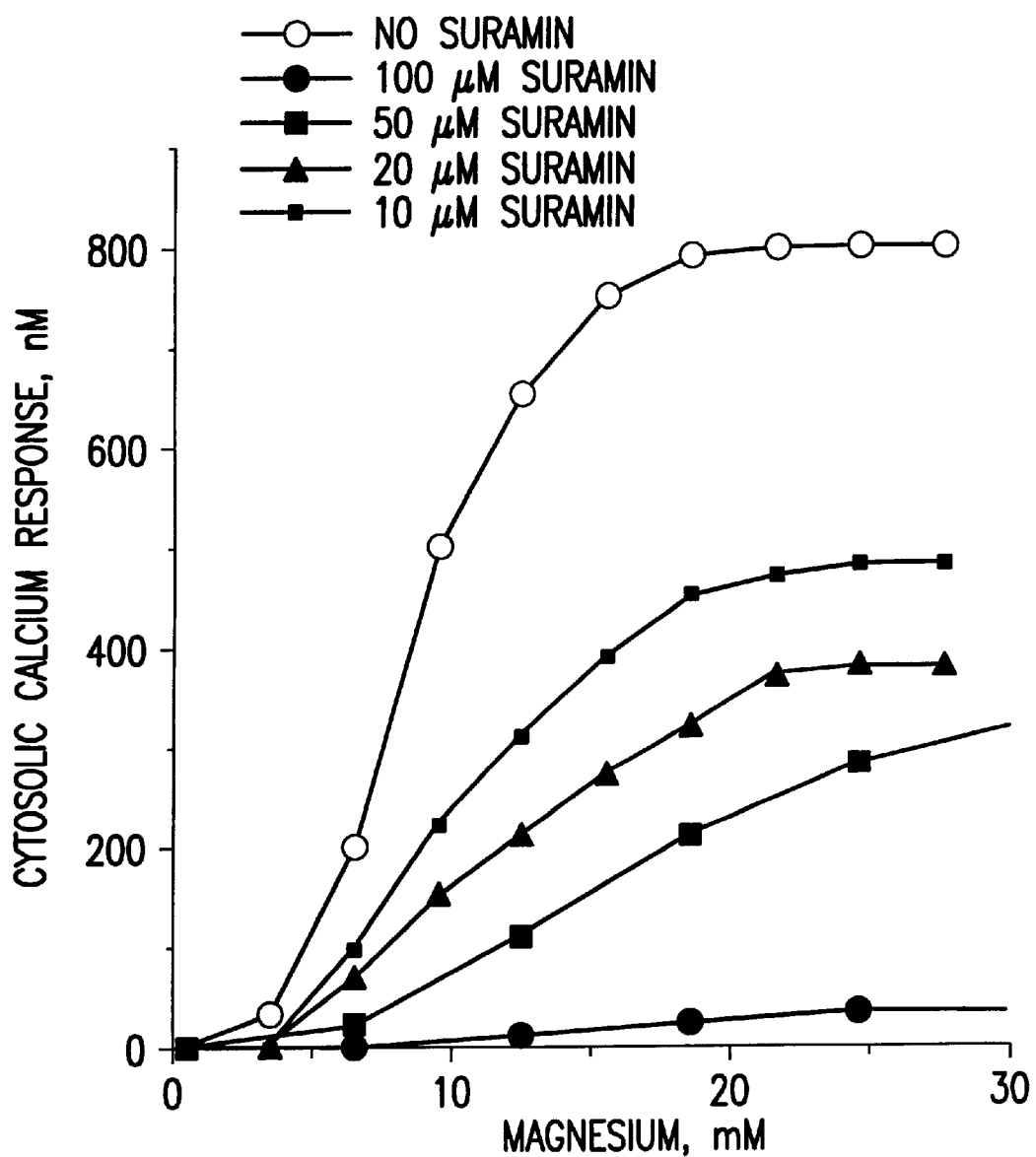
FIG. 17: Effect of suramin on CaR responsiveness to extracellular magnesium: The experiment of FIG. 16 was repeated using extracellular magnesium and concentrations of suramin ranging from 10 to 100 µM. Suramin was found to decrease the responsiveness of the cells in a dose-dependent manner.

Effect of suramin on CaR activation by calcium and magnesium: The effect of the small organic polyanion, suramin, on the cytosolic calcium response of CaR-transfected HEK cells to changes in external calcium concentration was studied and results are shown in FIGS. 16a and 16b. It can be seen that suramin at concentrations of 17 to 100 μM progressively decreases both the peak cytosolic response as well as the $EC_{50}$ of calcium. Similar results were found for magnesium (FIG. 17).

Discussion

The calcium-sensing receptor (CaR) is activated by agonists possessing multiple positive charges, including polyvalent cations (i.e. $Ca^{2+}$ and $Gd^{3+}$) and polycationic molecules (i.e. spermine and neomycin). Given this shared characteristic of CaR ligands, it is quite likely that these agonists act on the extracellular domain through an electrochemical mechanism, rather than a biochemical one. One possibility is that these cationic agonists may screen negatively charged residues of the extracellular domain, thus altering the conformation of the receptor. Indeed, multiple negative residues are grouped within this domain, particularly in the amino acid sequence of 126 to 251.

If screening of charge is an important mechanism of agonist action, then activation of the CaR should be modulated by ionic strength. The Debye length of the electrical field around the soluble polycationic ligand in inversely proportional to the square root of the ionic strength. With a decreased ionic strength and a longer Debye length, the polycationic ligands should be more effective at screening negatively charged residues of the extracellular domain. Furthermore, the positively and negatively charged residues could have a greater impact on the conformation of the receptor because their charge will not be screened as effectively by the reduced concentrations of monovalent ions present in the solution. Consistent with this model, decreased ionic strength allowed for more effective activation of the CaR by both $Ca^{2+}$ and spermine. Likewise an increase in ionic strength and a decrease in the Debye length attenuates the actions of $Ca_o$ and spermine as if the affinity of the agonist for the receptor had been reduced.

The effect of ionic strength on the activation of the CaR depends, in part, on the agonist under investigation. The shift in the $EC_{50}$ for activation by $Ca_o$ appeared linear and was approximately 0.2 mM per 10 mM change in ionic strength. The effects on CaR activation by spermine were less linear with a 20 mM change in ionic strength from basal solutions producing at least a 35% shift in $EC_{50}$ for spermine. While other ligands were not tested, it is likely that the greater the number of positive charges on the given agonist, the greater will be the effect of ionic strength on the agonist's activation of the CaR. This conclusion may be important in the brain. Extracellular polyamine levels are high and polyamines may be released in synaptic regions during neuronal stimulation. Furthermore, the ionic composition of the extracellular solution around the neuron and, in particular, the synapses can change dramatically during neuronal activity.

Initial studies varied NaCl in order to change the ionic strength of the media. However, other salts were tested which differed in the cationic or anionic species including ions with different predicted membrane permeabilities. In all cases, there were shifts in the activation of the CaR by $Ca_o$ similar in magnitude to that elicited by NaCl. There was little difference in the effects of salts when the cation was varied but the anion remained as chloride. Changing the chloride for anion species with molar solubility for the calcium salt yielded similar results. Only NaCl was tested for effects of decreases in ionic strength, as these were the principal ions in the standard Hepes-buffered solution; however there are no data suggesting that a separate mechanism exists to explain the effects of decreased versus increased ionic strength. Effects of osmolality cannot account for the modulation seen with ionic strength, since experiments using isosmotic solutions with different ionic strengths gave results similar to solutions where NaCl was simply added or removed without replacement by an uncharged osmolyte.

In summary, the CaR can sense changes in ionic strength independently of alterations in osmolality and the ionic species used to alter ionic strength. Ionic strength is related inversely to the efficacy of polycationic agonist activation of the receptor. Changes in ionic strength appear to modulate the different classes of CaR agonists in a similar manner. The ability of ionic strength to modify CaR function appears to be related to the mode of agonist activation, which likely involves screening of charged residues on the extracellular domain of the receptor. Modulation of CaR activation by ionic strength could have a particularly important physiological impact in the kidney, brain and intestines, where calcium regulation can be linked to sodium and water handling.

When a small organic polyanion, suramin, was used in experiments, it was found that the responsiveness of the CaR to both external concentrations of calcium and magnesium decreased substantially. By antagonizing the effect of extracellular calcium, suramin and similar polyanions should lead to an increase in the serum concentration of calcium in vivo.

All references cited are fully incorporated by reference. Having now fully described the invention, it will be understood by those of skill in the art that the invention may be performed within a wide and equivalent range of conditions, parameters, and the like, without affecting the spirit or scope of the invention or any embodiment thereof.

What is claimed is:

1. A polynucleotide consisting of a nucleotide sequence encoding the protein of SEQ ID NO:2.

2. A nucleic acid comprising the polynucleotide of claim 1.

3. The nucleic acid of claim 2, wherein said polynucleotide is operably linked to a promoter active in avian cells.

4. A host cell transformed with the nucleic acid of claim 3.

5. The polynucleotide of claim 1, wherein said polynucleotide has a nucleotide sequence consisting of that of SEQ ID NO:1.

6. A nucleic acid comprising the polynucleotide of claim 5.

7. The nucleic acid of claim 6, wherein said polynucleotide is operably linked to a promoter active in avian cells.

8. A host cell transformed with the nucleic acid of claim 7.

9. A DNA construct comprising the polynucleotide of claim 1, but wherein one or more nucleotides of codon 127 have been replaced by a different nucleotide.

10. The DNA construct of claim 9, wherein said polynucleotide is operably linked to a promoter active in avian cells.

* * * * *